(12) United States Patent
Ohno et al.

(10) Patent No.: US 11,436,871 B2
(45) Date of Patent: Sep. 6, 2022

(54) LIVING BODY DETERMINATION DEVICE, LIVING BODY DETERMINATION METHOD, AND LIVING BODY DETERMINATION PROGRAM

(71) Applicant: NEC Corporation, Tokyo (JP)

(72) Inventors: Yuji Ohno, Tokyo (JP); Masahiro Kubo, Tokyo (JP); Katsumi Abe, Tokyo (JP); Ersin Altintas, Tokyo (JP); Takeshi Akagawa, Tokyo (JP); Tetsuri Ariyama, Tokyo (JP)

(73) Assignee: NEC CORPORATION, Tokyo (JP)

( * ) Notice: Subject to any disclaimer, the term of this patent is extended or adjusted under 35 U.S.C. 154(b) by 208 days.

(21) Appl. No.: 16/857,680

(22) Filed: Apr. 24, 2020

(65) Prior Publication Data
US 2020/0250449 A1 Aug. 6, 2020

Related U.S. Application Data

(62) Division of application No. 15/753,604, filed as application No. PCT/JP2016/067124 on Jun. 8, 2016, now abandoned.

(30) Foreign Application Priority Data

Sep. 3, 2015 (JP) ................................ 2015-173737

(51) Int. Cl.
*A61B 5/00* (2006.01)
*G06V 10/143* (2022.01)
(Continued)

(52) U.S. Cl.
CPC ............ *G06V 40/45* (2022.01); *A61B 5/0075* (2013.01); *A61B 5/1171* (2016.02);
(Continued)

(58) Field of Classification Search
None
See application file for complete search history.

(56) References Cited

U.S. PATENT DOCUMENTS

2003/0202687 A1 10/2003 Hamid et al.
2005/0271258 A1 12/2005 Rowe
(Continued)

FOREIGN PATENT DOCUMENTS

| JP | 2006-242909 A | 9/2006 |
|---|---|---|
| JP | 2009-182445 A | 8/2009 |

(Continued)

OTHER PUBLICATIONS

Nixon, K.—"Spoof Detection Schemes"—Springer 2007, pp. 1-16 (Year: 2007).*

(Continued)

*Primary Examiner* — Bernard Krasnic
(74) *Attorney, Agent, or Firm* — Sughrue Mion, PLLC

(57) ABSTRACT

A living body determination device includes: a light irradiation device that irradiates a measuring object with a first light including a plurality of spectrums; a spectroscopic device that disperses a light at intensity depending on a wavelength and outputs the light; an image acquisition device that receives the light output by the spectroscopic device and outputs image information representing brightness depending on the intensity of the light; and a control unit. The control unit, for each spectrum of the first light, acquires image information with respect to the measuring object from the image acquisition device, based on the image information, selects one or more areas, for each of the areas, acquires spectroscopic information, and based on whether the spectroscopic information satisfies a predetermined condition, determines whether the measuring object is a living body.

7 Claims, 32 Drawing Sheets

(51) Int. Cl.

| | |
|---|---|
| *G06V 40/40* | (2022.01) |
| *A61B 5/1171* | (2016.01) |
| *G06V 10/60* | (2022.01) |
| *G06V 10/88* | (2022.01) |
| *G06V 10/141* | (2022.01) |
| *G06V 40/16* | (2022.01) |
| *G06V 40/12* | (2022.01) |
| *G01J 3/28* | (2006.01) |
| *G06F 21/32* | (2013.01) |

(52) U.S. Cl.
CPC .......... *A61B 5/1176* (2013.01); *G01J 3/2823* (2013.01); *G06F 21/32* (2013.01); *G06V 10/141* (2022.01); *G06V 10/143* (2022.01); *G06V 10/60* (2022.01); *G06V 10/89* (2022.01); *G06V 40/1382* (2022.01); *G06V 40/166* (2022.01); *G06V 40/169* (2022.01)

(56) References Cited

U.S. PATENT DOCUMENTS

| | | |
|---|---|---|
| 2008/0192988 A1 | 8/2008 | Uludag et al. |
| 2009/0080709 A1 | 3/2009 | Rowe et al. |
| 2009/0318815 A1 | 12/2009 | Barnes et al. |
| 2010/0141380 A1 | 6/2010 | Pishva |
| 2010/0165090 A1 | 7/2010 | Sweeney et al. |
| 2011/0170750 A1 | 7/2011 | Kropp et al. |
| 2012/0314048 A1 | 12/2012 | Matos |
| 2013/0150687 A1 | 6/2013 | Kato |
| 2015/0254495 A1 | 9/2015 | Rowe et al. |
| 2016/0012599 A1 | 1/2016 | Kuboyama |
| 2018/0173976 A1 | 6/2018 | Hama et al. |
| 2018/0173979 A1* | 6/2018 | Fan ...................... G06K 9/2036 |
| 2018/0220939 A1* | 8/2018 | Matsuo ................ G06K 9/4652 |

FOREIGN PATENT DOCUMENTS

| | | | |
|---|---|---|---|
| JP | 2009-544108 A | 12/2009 | |
| JP | 4844939 B2 | 12/2011 | |
| JP | 2014-184002 A | 10/2014 | |
| WO | WO-2009110323 A1 * | 9/2009 | ......... G06K 9/00906 |

OTHER PUBLICATIONS

International Search Report for PCT Application No. PCT/JP2016/067124, dated Jul. 12, 2016.

English translation of Written opinion for PCT Application No. PCT/JP2016/067124, dated Jul. 12, 2016.

* cited by examiner

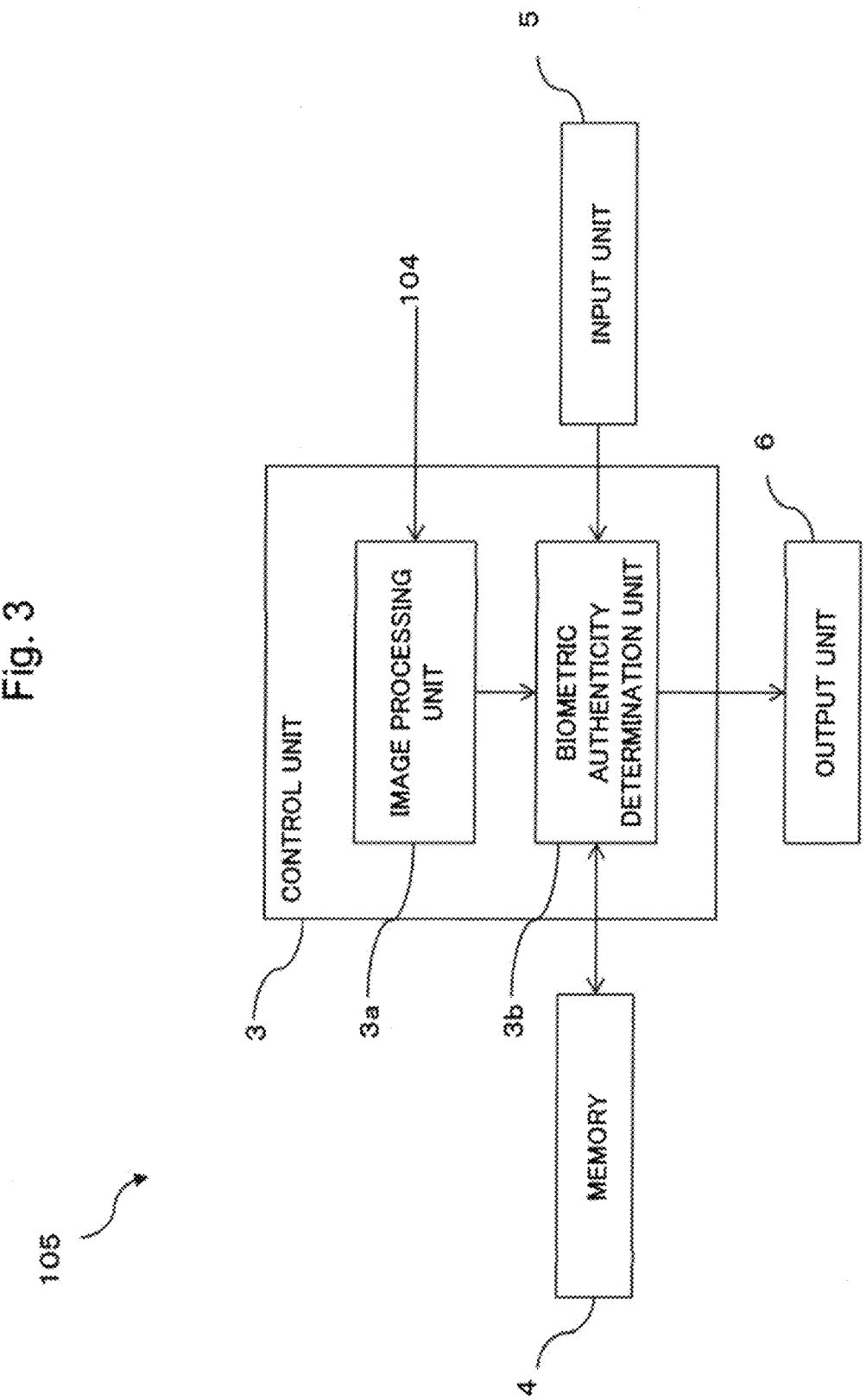

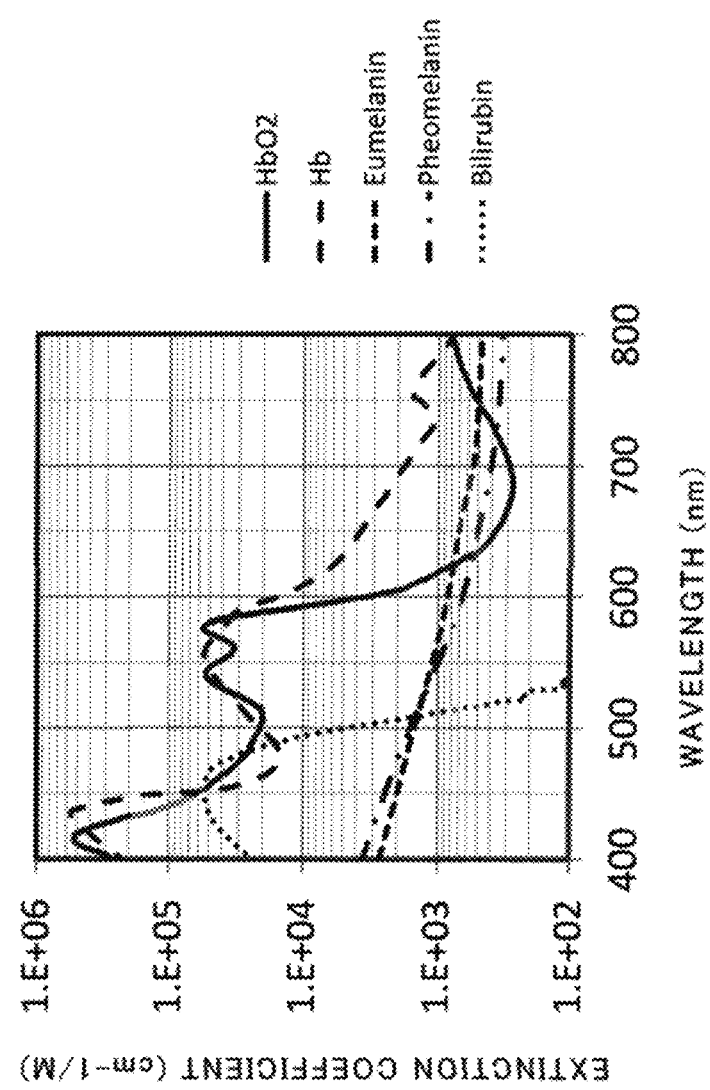

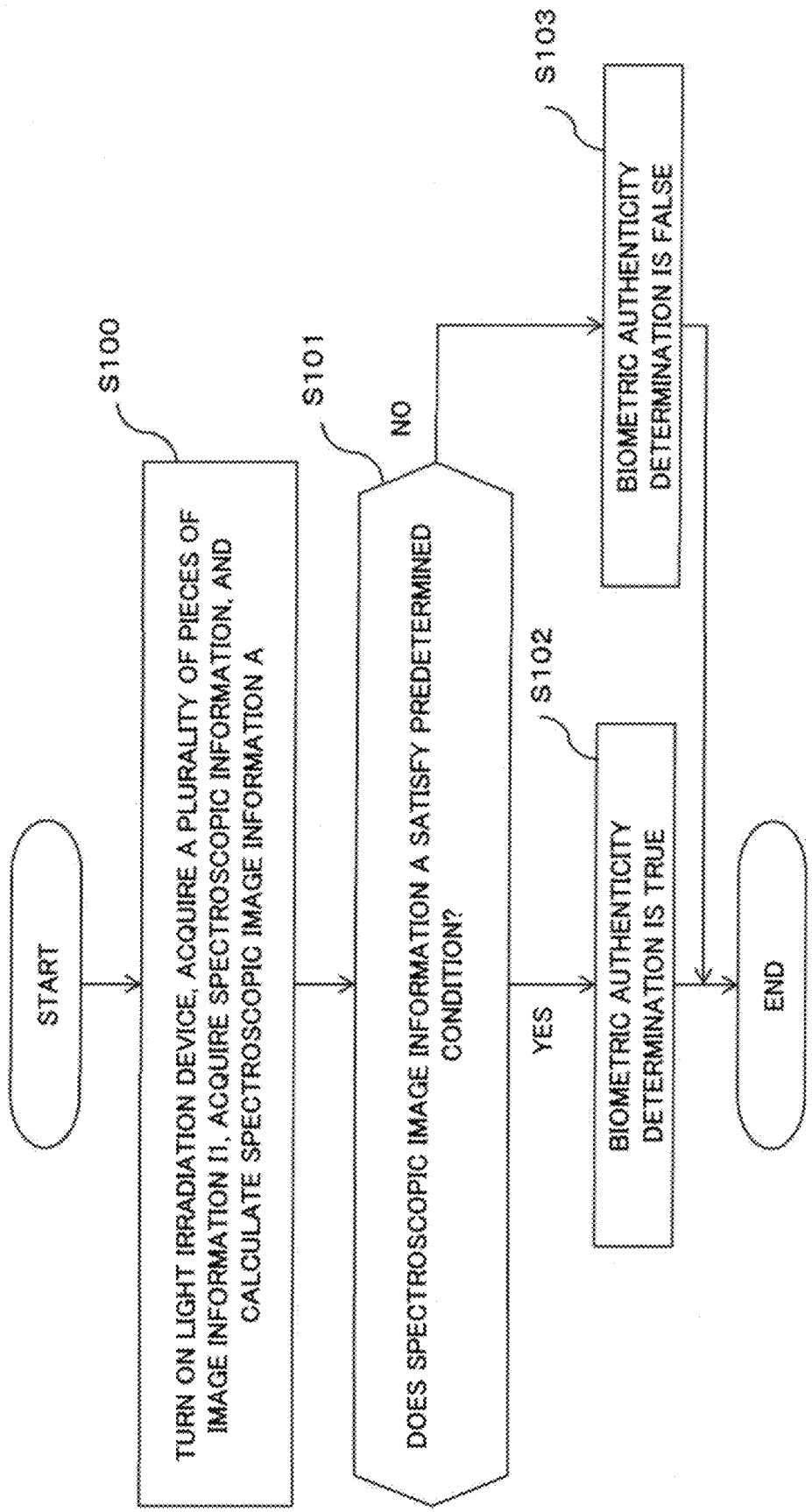

LIVING BODY DETERMINATION DEVICE, LIVING BODY DETERMINATION METHOD, AND LIVING BODY DETERMINATION PROGRAM

The present application is a divisional application of Ser. No. 15/753,604 filed on Feb. 20, 2018, which is a National Stage Entry of PCT/JP2016/067124 filed on Jun. 8, 2016, which claims priority from Japanese Patent Application 2015-173737 filed on Sep. 3, 2015, the contents of all of which are incorporated herein by reference, in their entirety.

TECHNICAL FIELD

The disclosed subject matter relates to a living body determination device, a living body determination method and a living body determination program for determining whether a measuring object is a living body. Further, the disclosed subject matter relates to a biometric authentication device, a biometric authentication method and a biometric authentication program to which such living body determination is applied.

BACKGROUND ART

Provided are various devices and systems having a biometric authentication function for conducting a biometric authentication using a biological information representing physical features such as a fingerprint and a face. However, since there has been a case where a counterfeit physical feature (for example, printed material or tablet terminal, counterfeit (face mask)) is erroneously determined as a real thing, a reliability of the biometric authentication has not been sufficiently high.

Thus, as a countermeasure against an unauthorized authentication using a false finger or the like, a living body determination for determining whether the measuring object is the living body is conducted. For example, PTLs 1 and 2 disclose a device and a system that conduct the living body determination and the biometric authentication.

A biological detection device disclosed in PTL 1 detects whether an object is a living body based on whether a pulse wave is detected.

A multi-factor authentication system disclosed in PTL 2 includes non-spectrometric biometric information acquisition means for capturing an image of a finger and acquiring a fingerprint image and spectroscopic biometric information acquisition means for acquiring a diffuse reflectance spectrum from a finger. Based on the diffuse reflectance spectrum from the finger, whether an object to be authenticated is a living body having predetermined spectroscopic characteristics is determined.

CITATION LIST

Patent Literature

PTL 1: Japanese Unexamined Patent Publication No. 2014-184002
PTL 2: Japanese Patent Publication No. 4844939

SUMMARY OF INVENTION

Technical Problem

However, the devices and the systems disclosed in PTLs 1 and 2 have the following problems.

In the biological detection device disclosed in PTL 1, when a thin counterfeit is mounted and when the tablet terminal displays a face image, a pulse is detected and it is possible that an object is erroneously determined as a living body.

In the multi-factor authentication system disclosed in PTL 2, in a living body determination based on the diffuse reflectance spectrum from the living body (finger), for example, when the counterfeit is pasted to a part of the living body, there is a case where a fragment of a film-like counterfeit is overlooked. Further, when the system is applied to a face authentication, due to effects of a hair, eyes, a wrinkle, a mole, a lip and the like other than a skin, it is possible that a determination is erroneously made that an object is not a living body.

A purpose of the disclosed subject matter is to solve each of the above described problems, and to provide a living body determination device, a living body determination method and a living body determination program that can detect the thin counterfeit, the tablet terminal, and the fragment of the counterfeit and can determine the living body without receiving influences of materials other than the skin.

Another purpose of the disclosed subject matter is to provide a biometric authentication device, a biometric authentication method and a biometric authentication program that can improve the reliability of the biometric authentication and enable ensuring of high degree of security.

Solution to Problem

In order to achieve the above purpose, according to one aspect of the disclosed subject matter, a living body determination device includes: light irradiation means for irradiating a measuring object with a first light including a plurality of spectrums; spectroscopic means for dispersing a light at intensity depending on a wavelength and outputting the light; image acquisition means for receiving the light output by the spectroscopic means and outputting image information representing brightness depending on the intensity of the light; and a control unit that. For each spectrum of the first light, the control unit acquires image information with respect to the measuring object from the image acquisition means, based on the image information, selects one or more areas, for each of the areas, acquires spectroscopic information, and based on whether the spectroscopic information satisfies a predetermined condition, determines whether the measuring object is a living body.

According to another aspect of the disclosed subject matter, a living body determination method is conducted at a device including light irradiation means for irradiating a measuring object with a first light including a plurality of spectrums, spectroscopic means for dispersing a light at intensity depending on a wavelength and outputting the light, and image acquisition means for receiving the light output by the spectroscopic means and outputting image information representing brightness depending on the intensity of the light. The living body determination method includes: for each spectrum of the first light, acquiring image information with respect to the measuring object from the image acquisition means; based on the image information, selecting one or more areas and for each of the areas, acquiring spectroscopic information; and based on whether the spectroscopic information satisfies a predetermined condition, determining whether the measuring object is a living body.

According to further another aspect of the disclosed subject matter, a living body determination program for causing a computer of a device that includes light irradiation means for irradiating a measuring object with a first light including a plurality of spectrums, spectroscopic means for dispersing a light at intensity depending on a wavelength and outputting the light, and image acquisition means for receiving the light output by the spectroscopic means and outputting image information representing brightness depending on the intensity of the light, to execute the processes of: for each spectrum of the first light, acquiring image information with respect to the measuring object from the image acquisition means; based on the image information, selecting one or more areas and for each of the areas, acquiring spectroscopic information; and based on whether the spectroscopic information satisfies a predetermined condition, determining whether the measuring object is a living body.

In order to achieve the above purpose, a biometric authentication device including: light irradiation means for irradiating a measuring object with a first light including a plurality of spectrums; spectroscopic means for dispersing a light at intensity depending on a wavelength and outputting the light; image acquisition means for receiving the light output by the spectroscopic means and outputting image information representing brightness depending on the intensity of the light; and a control unit that, for each spectrum of the first light, acquires image information with respect to the measuring object from the image acquisition means, based on the image information, selects one or more areas, acquires spectroscopic information for each of the areas, and based on whether the spectroscopic information satisfies a predetermined condition, determines whether the measuring object is a living body. The control unit, when the measuring object is determined to be a living body, acquires, from the image information, biological information representing a physical feature, determines whether the biological information matches with authentication biometric information registered in advance, when the biological information matches with the authentication biometric information registered in advance, determines that an authentication is successful, and when the biological information does not match with the authentication biometric information registered in advance, determines that an authentication is not successful.

According to another aspect to a biometric authentication method is conducted at a device including light irradiation means for irradiating a measuring object with a first light including a plurality of spectrums, spectroscopic means for dispersing a light at intensity depending on a wavelength and outputting the light, and an image acquisition means for receiving the light output by the spectroscopic means and outputting image information representing brightness depending on the intensity of the light. The biometric authentication method includes: for each spectrum of the first light, acquiring image information with respect to the measuring object from the image acquisition means; based on the image information, selecting one or more areas and for each of the areas, acquiring spectroscopic information; based on whether the spectroscopic information satisfies a predetermined condition, determining whether the measuring object is a living body; and when the measuring object is determined to be a living body, acquiring, from the image information, biological information representing a physical feature, determining whether the biological information matches with authentication biometric information registered in advance, when the biological information matches with the authentication biometric information registered in advance, determining that an authentication is successful, and when the biological information does not match with the authentication biometric information registered in advance, determining that an authentication is not successful.

According to further aspect to the disclosed subject matter, a biometric authentication program for causing a computer of a device that includes light irradiation means for irradiating a measuring object with a first light including a plurality of spectrums, spectroscopic means for dispersing a light at intensity depending on a wavelength and outputting the light, and an image acquisition means for receiving the light output by the spectroscopic means and outputting image information representing brightness depending on the intensity of the light, to execute the processes of: for each spectrum of the first light, acquiring image information with respect to the measuring object from the image acquisition means; based on the image information, selecting one or more areas and for each of the areas, acquiring spectroscopic information; based on whether the spectroscopic information satisfies a predetermined condition, determining whether the measuring object is a living body; and when the measuring object is determined to be a living body, acquiring, from the image information, biological information representing a physical feature, determining whether the biological information matches with authentication biometric information registered in advance, when the biological information matches with the authentication biometric information registered in advance, determining that an authentication is successful, and when the biological information does not match with the authentication biometric information registered in advance, determining that an authentication is not successful.

BRIEF DESCRIPTION OF DRAWINGS

FIG. 3 is a block diagram illustrating a configuration of a computing device of the living body determination device illustrated in FIG. 1.

FIG. 5 is a characteristic diagram illustrating one example of a spectrum of a component part with respect to the living body.

FIG. 6 is a flowchart illustrating one procedure of a biometric determination operation of the living body determination device illustrated in FIG. 1.

DESCRIPTION OF EMBODIMENTS

Next, example embodiments of the disclosed subject matter are described with reference to drawings.

First Example Embodiment

Figure 1:
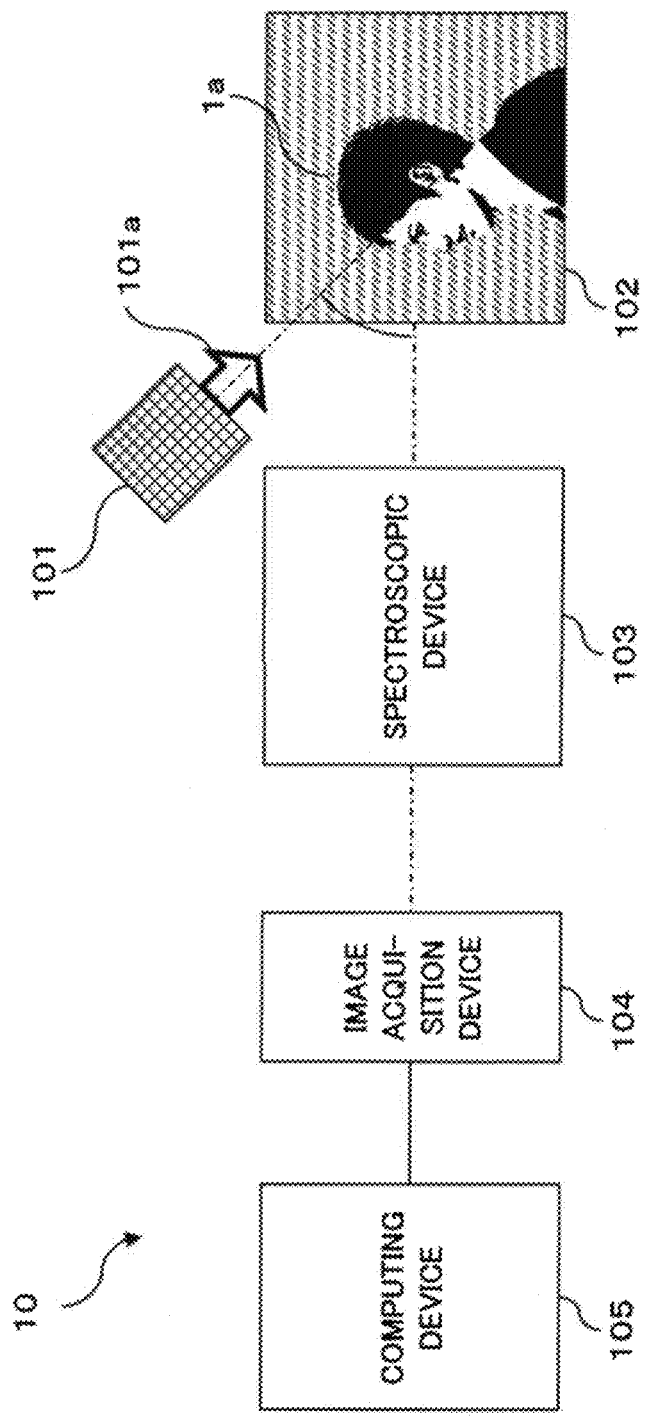
FIG. 1 is a block diagram illustrating a configuration of a living body determination device according to a first example embodiment of the disclosed subject matter.

FIG. 1 is a block diagram illustrating a configuration of a living body determination device according to a first example embodiment of the disclosed subject matter.

With reference to FIG. 1, a living body determination device 10 includes a light irradiation device 101, a target installation device 102, a spectroscopic device 103, an image acquisition device 104, and a computing device 105.

The target installation device 102 is a target installation unit that places a position of a measuring object 1a within a predetermined range. For example, the target installation device 102 includes an image capture box, a seat to sit an object person to be measured, and a display unit used for instructing a position to stand to the object person to be measured. Herein, the measuring object 1a is a part of a body (for example, an upper body, a cephalic region, a face and the like). FIG. 1 schematically illustrates the cephalic region as one example of the measuring object 1a.

The light irradiation device 101 irradiates the target installation device 102 with light 101a. The light irradiation device 101 is positioned so as to irradiate the measuring object 1a from the front. When the target installation device 102 is viewed from a vertical direction, an optical axis of the light irradiation device 101 and an optical axis of the spectroscopic device 103 cross at an angle θ. Although the angle θ can be appropriately set, the angle is preferably less than 90 degrees. The light irradiation device 101 includes a light source having a plurality of spectrums within a wavelength range that is from a visible light region to a near infrared light region and an optical system for directing light emitted from the light source toward a direction of the target installation device 102. The visible light region is generally a wavelength region from 380 nm to 780 nm and the near infrared light region is generally a wavelength region from 700 nm to 2500 nm. As the light source of the light irradiation device 101, for example, a white LED obtained by combining a monochromatic LED (Light Emitting Diode) with fluorescent materials, a light source that includes a plurality of light-emitting elements (for example, LED) having different emission wavelengths, a halogen lamp, a xenon lamp and the like can be used. Further, as the light source of the light irradiation device 101, a light source including an optical filter that allows transmission of only a specific wavelength can be used.

The light 101a from the light irradiation device 101 is reflected or scattered at the measuring object 1a, and as a result, from adjacent of the target installation device 102, lights are emitted to various directions. A part of radiated lights (reflected light and scattered light) from the adjacent of the target installation device 102 is directed to a direction of the spectroscopic device 103.

The spectroscopic device 103 receives, from a side of the target installation device 102, the light, disperses the received light to the intensity depending on the wavelength, and outputs the dispersed light. The light output by the spectroscopic device 103 is supplied to the image acquisition device 104. As the spectroscopic device 103, for example, a dispersive spectroscopic device, the Fourier transform spectrometer, a liquid crystal band-pass filter, a device for controlling an irradiation order when the light irradiation device 101 is a light source that includes a plurality of light-emitting elements having different emission wavelengths (hereinafter referred to as "light irradiation order control device") and the like may be used.

The Fourier transform spectrometer gives, to the incident light, the spatial phase difference and emits the interference wave (interferogram). Specifically, the Fourier transform spectrometer has, on the optical Fourier transform plane, the phase variable filter (for example, movable mirror) and by operating the phase variable filter, gives, to the incident light, the spatial phase difference. By giving, to the incident light, the spatial phase difference, an imaging state in an image acquisition device 105 changes. An imaging intensity distribution changes depending on the given spatial phase difference. Here, by changing the spatial phase difference in a phased manner or continuously, the interferogram can be acquired.

Figure 2:
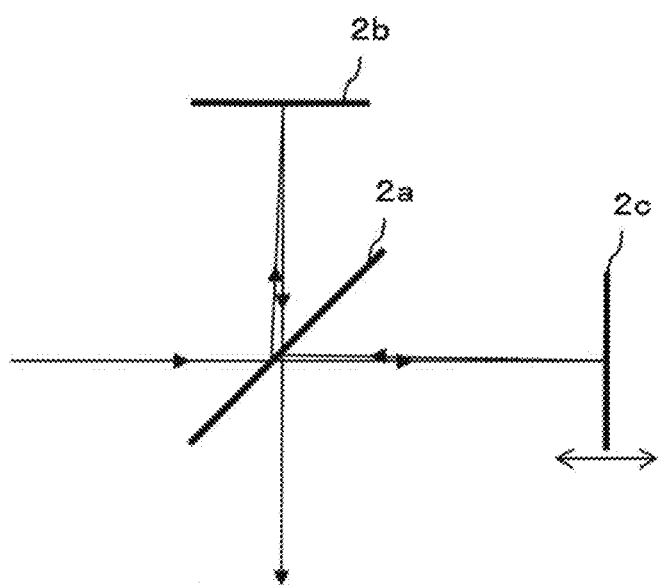
FIG. 2 is a schematic diagram illustrating a configuration of Fourier transform spectrometer used for the living body determination device illustrated in FIG. 1.

FIG. 2 illustrates one example of the Fourier transform spectrometer. The Fourier transform spectrometer includes a half mirror 2a, a fixed mirror 2b and a movable mirror 2c. The radiated light (incident light) from the adjacent of the seating enters the half mirror 2a. The light reflected at the half mirror 2a (first light) is reflected at the fixed mirror 2b, and again enters the half mirror 2a. The light that transmits the half mirror 2a (second light) is reflected at the movable mirror 2c, and again enters the half mirror 2a. Among reflected lights (first light) from the fixed mirror 2b, the light that transmits the half mirror 2a and among reflected lights (second light) from the movable mirror 2c, the light reflected at the half mirror 2a are superimposed with each other and output on the same optical path. By moving the movable mirror 2c back and forth, a phase difference is given between the first light and the second light.

As another example of the Fourier transform spectrometer, the wave surfaces of the incident light are divided, to one of divided lights, any phase difference is given, and then the superimposed again.

The dispersive spectroscopic device diverges the incident lights depending on the wavelength and emits in sequence the separated lights for each wavelength. The dispersive spectroscopic device includes a prism spectroscope or a grating spectroscope. As one example, a configuration of the grating spectroscope is described.

The grating spectroscope includes an entrance slit, an exit slit, first and second spherical mirrors and a diffraction grating. The entrance slit is positioned at a focal point of the first spherical mirror and the exit slit is positioned at a focal point of the second spherical mirror. With the light entering through the entrance slit, via the first spherical mirror, the diffraction grating is irradiated. The first spherical mirror converts the incident light from the entrance slit to the parallel light. The parallel light that is diffracted by the diffraction grating at an angle depending on the wavelength, via the second spherical mirror, is imaged on the exit slit. By rotating the diffraction grating, the wavelength of the light emitted from the exit slit changes.

The liquid crystal band-pass filter includes a liquid crystal, polarizer, and the analyzer. By applying voltage to the liquid crystal, a transmission wavelength is controlled. By configuring the filter with a plurality of liquid crystals, the polarizer, and the analyzer, a half band width of the transmission wavelength can be controlled. By adding a phase difference plate to a configuration, a chromatic dispersion may be controlled.

The image acquisition device 104 is a device that can acquire two-dimensional image information. As the image acquisition device 104, for example, a CCD (charge-coupled device) image sensor, a CMOS (complementary metal oxide semiconductor) image sensor, an InGaAs (Indium Gallium Arsenide) image sensor, a CIGS (copper indium gallium selenide) image sensor and the like can be used. The light output from the spectroscopic device 103 is imaged on a light receiving surface of the image acquisition device 104. The image acquisition device 104 outputs the two-dimensional image information in which the light output from the spectroscopic device 103 is converted to lightness information representing a tone of a color depending on the intensity thereof. The two-dimensional image information output from the image acquisition device 104 is supplied to the computing device 105.

The computing device 105 controls a lighting operation of the light irradiation device 101 and a spectroscopic operation of the spectroscopic device 103, acquires, from the image acquisition device 104, the image information, and conducts image processing and biometric authenticity determination processes. The computing device 105 can be configured, for example, using a computer device or the like which operates in accordance with a program.

When the spectroscopic device 103 is the dispersive spectroscopic device, the computing device 105 causes the spectroscopic device 103 to diverge the incident lights depending on the wavelength and to conduct spectroscopic operations of emitting the separated lights in sequence for each wavelength. For example, when the spectroscopic device 103 is the grating spectroscope, by controlling rotational operations of the diffraction grating, the computing device 105 causes the grating spectroscope to emit the separated lights in sequence for each wavelength.

When the spectroscopic device 103 is the Fourier transform spectrometer, the computing device 105 causes the spectroscopic device 103 to give, to the entered light, the spatial phase difference and to conduct the spectroscopic operations of emitting the interference wave (interferogram). For example, when the spectroscopic device 103 is the Fourier transform spectrometer illustrated in FIG. 2, the computing device 105, by moving the movable mirror 2c in a phased manner or continuously, causes the Fourier transform spectrometer to emit the interference wave (interferogram).

When the spectroscopic device 103 is the liquid crystal band-pass filter, the computing device 105 causes the spectroscopic device 103 to change the voltage and to conduct the spectroscopic operation of emitting the separated lights in sequence for each wavelength.

Note that positions of the spectroscopic device 103 and an image device 104 are not limited to illustrated positions. The spectroscopic device 103 and the image device 104 does not necessarily need to be positioned at the vertical direction of the target installation device 102, but may be positioned at a direction tilting from the target installation device 102.

FIG. 3 illustrates a configuration of the computing device 105. Referring to FIG. 3, the computing device 105 includes a control unit 3, a memory 4, an input unit 5 and an output unit 6.

The memory 4 is a storage device such as a HDD (hard disk drive) and a semiconductor memory and stores the living body determination program and data that are necessary for conducting the image processing and the biometric authenticity determination process. The living body determination program is a program for causing a computer (CPU (Central Processing Unit) or the like) to conduct the image processing and the biometric authenticity determination process. The living body determination program may be supplied via a communication network (for example, internet) or may be supplied from a computer-readable recording medium. The computer-readable recording medium includes, for example, optical disks such as a CD (Compact Disc) and a DVD (Digital Versatile Disc), a USB (Universal Serial Bus) memory, a memory card and the like.

The output unit 6 is a display device such as a liquid crystal display and a sound output device such as a speaker. The input unit 5 includes a keyboard, a sound input device and the like. When the output unit 6 is a display device, as the input unit 5, a touch panel provided on a display screen may be used.

The control unit 3 includes the CPU that operates in accordance with the program, receives an operator guidance from the input unit 5, controls the lighting operation of the light irradiation device 101 and the spectroscopic operation of the spectroscopic device 103, and conducts the image processing and the biometric authenticity determination process. The control unit 3 includes an image processing unit 3a and a biometric authenticity determination unit 3b.

The image processing unit 3a, during a period in which the light irradiation device 101 is lighted, controls the spectroscopic operation of the spectroscopic device 103, and acquires, from the image acquisition device 104, a plurality of pieces of image information I1 with respect to the measuring object 1a. Here, the plurality of pieces of image information I1 are pieces of image information for each wavelength of light reflected or scattered at the measuring object 1a among the lights 101a emitted from the light irradiation device 101. In other words, the plurality of pieces of image information I1 are pieces of image information that are acquired for each spectrum with respect to each spectrum of the light 101a.

The number of pieces of the image information I1 is determined depending on the wavelength resolution of a spectroscopic device 104. For example, when the wavelength rang from the light irradiation device 101 to the light 101a is 500 nm to 800 nm, the acquisition wavelength range of the spectroscopic device 104 is 500 nm to 800 nm, and the wavelength resolution is 5 nm, as the pieces of image information I1, from 500 nm to 800 nm, in 5 nm increments, 61 pieces of two-dimensional image information are acquired.

The image processing unit 3a, from the plurality of pieces of image information I1, acquires spectroscopic information at predetermined areas of the image, and calculates spectroscopic image information A. Here, the spectroscopic information represents the wavelength dependence of the intensity at predetermined areas of the image. The predetermined area is any site (range of specific pixel) of the measuring object 1a in the image and can be set in advance.

Figure 4A:
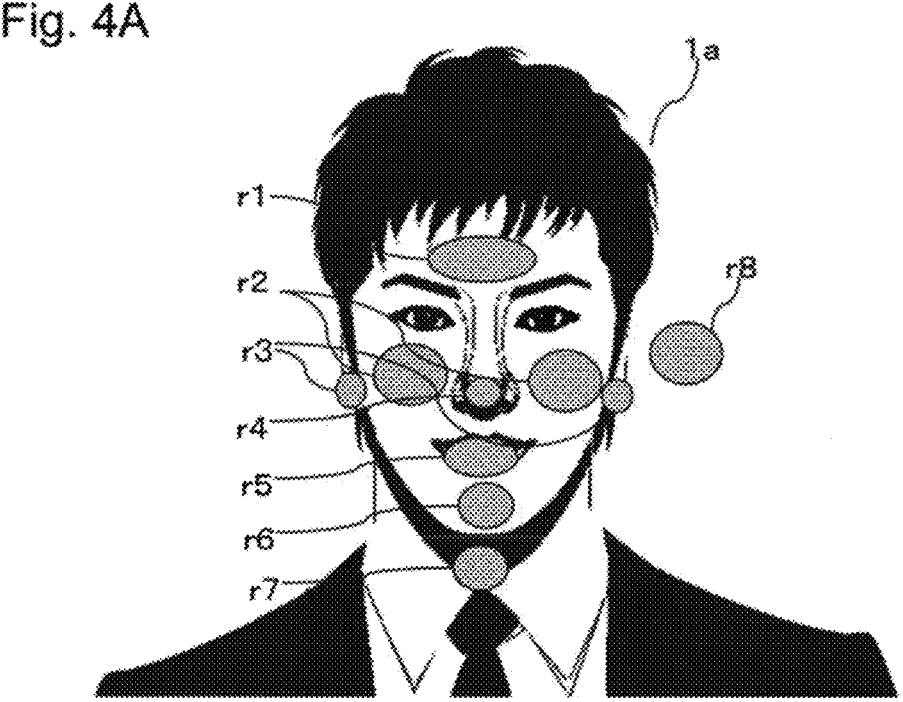
FIG. 4A is a schematic diagram illustrating one example of a predetermined area in a single piece of total image information obtained by integrating a plurality of pieces of image information.

As one example, FIG. 4 illustrates the predetermined areas of the image. FIG. 4A illustrates a single piece of total image information obtained by integrating the plurality of pieces of image information I1. Here, although the image of the face is schematically illustrated, the image is created for explanations, and the image is different from an actual image. FIG. 4A illustrates, as examples of the predetermined areas, r1(forehead), r2(cheek), r3(*ear*), r4(nose), r5(*lip*), r6(*jaw*), r7(neck), and r8(in vitro).

Figure 4B:
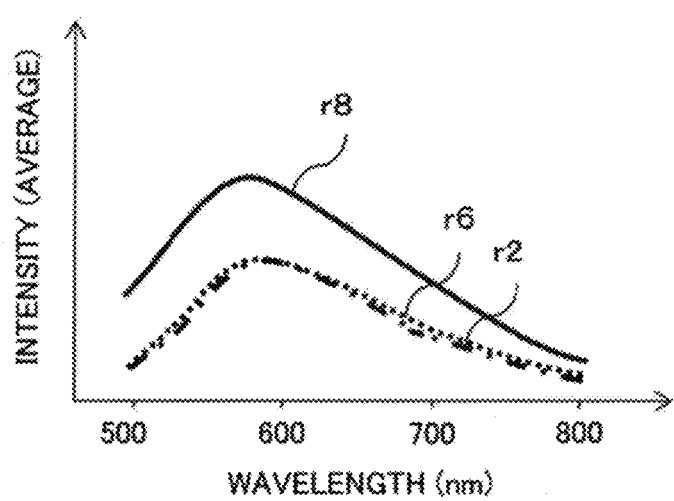
FIG. 4B is a characteristic diagram illustrating a wavelength dependence of intensity at the predetermined areas of the total image information illustrated in FIG. 4A.

FIG. 4B is a graph representing the wavelength dependence of the intensities at r2, r6 and r8 respectively among the predetermined areas of the total image information of the face illustrated in FIG. 4A. As the light irradiation device 101, the white LED is used, as the spectroscopic device 103, the grating spectroscope is used, and as the image acquisition device 104, the CMOS image sensor is used.

The image processing unit 3a, based on the total image information, selects one or more areas and for each area, acquires the spectroscopic information. In other words, the image processing unit 3a acquires the spectroscopic information of the predetermined areas of the total image information with one or more areas. For example, among the predetermined areas, i.e., the areas r1 to r8 illustrated in FIG. 4A, when the areas related to sites representing the physical features are r1 to r7, the image processing unit 3a, among the areas r2, r6, and r8 illustrated in FIG. 4B, acquires pieces of spectroscopic information of the areas r2 and r6 respectively. Then, the image processing unit 3a calculates the spectroscopic image information A which is obtained by adding, to the spectroscopic information, each piece of image information I1.

Note that acquisition operations of the image information I1 are different between when the spectroscopic device 103 is the dispersive spectroscopic device, the liquid crystal band-pass filter, or the light irradiation order control device and when the spectroscopic device 103 is the Fourier transform spectrometer.

When the spectroscopic device 103 is the dispersive spectroscopic device, the liquid crystal band-pass filter, or the light irradiation order control device, the spectroscopic device 103 sequentially supplies the separated lights for each wavelength to the image acquisition device 104, and thus, the image acquisition device 104, for each wavelength, outputs the image information. In this case, the image processing unit 3a, for each piece of image information I1, acquires, from the image acquisition device 104, the image information of each wavelength.

On the other hand, when the spectroscopic device 103 is the Fourier transform spectrometer, the spectroscopic device 103 supplies the interference wave (interferogram) to the image acquisition device 104, and thus, the image acquisition device 104 outputs the image information representing the interferogram. In this case, the image processing unit 3a, for each piece of image information I1, conducts the Fourier transformation to the image information of the interferogram output from the image acquisition device 104, and thus, acquires the image information of each wavelength.

The spectroscopic image information A calculated by the image processing unit 3a is supplied to the biometric authenticity determination unit 3b. The biometric authenticity determination unit 3b, based on whether the spectroscopic information in the spectroscopic image information A satisfies the predetermined condition, makes the biometric authenticity determination as to whether the measuring object 1a is the living body.

The biometric authenticity determination unit 3b determines whether the absorbency of the spectroscopic image information A is higher than a predetermined value. Whether the absorbency is higher than the predetermined value can be determined depending on whether the reflectivity is lower than a predetermined value. When the absorbency is the predetermined value or more, the biometric authenticity determination unit 3b determines that the predetermined condition is satisfied. Alternatively, when the absorbency is smaller than the predetermined value, the biometric authenticity determination unit 3b determines that the predetermined condition is not satisfied.

Further, the biometric authenticity determination unit 3b compares the spectrum (spectroscopic information) of the spectroscopic image information A with the biological determination spectrum stored in the memory 4. The biological determination spectrum is obtained by combining spectrums with respect to the living body. The spectrum with respect to the living body is a spectrum of a component with respect to the living body such as, for example, Oxyhemoglobin, HbO2, Deoxyhemoglobin, Hb, Bilirubin, Eumelanin, Pheomelanin, water, carotene, fat, protein.

FIG. 5 illustrates, as one example of the spectrum of the component with respect to the living body, the absorption spectrum of Oxyhemoglobin, HbO2, Deoxyhemoglobin, Hb, Bilirubin, Eumelanin, and Pheomelanin. Here, the example of the spectrum approximately 36° C. is specially illustrated. Note that the spectrum with respect to the living body is not limited to the example illustrated in FIG. 5.

The combination of the spectrums with respect to the living body is, for example, a combination of absorption spectrums (wavelength dependence of extinction coefficient) of biometric components illustrated in FIG. 5. The combination of the spectrums with respect to the living body (combination of biometric components) can be calculated, for example, based on the equation 1 below.

[Mathematical 1]

$$A(\lambda) = \log_{10} \sum_i (a_i x_i(\lambda)^{p_i})$$  Equation 1

Here, $\lambda$ represents the wavelength, $a_i$ and $p_i$ represent coefficients (fitting parameters), and $x_i(\lambda)$ represents the wavelength dependence of the extinction coefficient of each biometric component. The $A(\lambda)$ that is calculated through the equation 1 represents the wavelength dependence of the absorbency.

The biometric authenticity determination unit 3b calculates the degree of correlation between the spectrum (spectroscopic information) of the spectroscopic image information A and the biological determination spectrum and determines whether the degree of correlation is the predetermined value or above. When the degree of correlation is the predetermined value or above, the biometric authenticity determination unit 3b determines that the predetermined condition is satisfied. Alternatively, when degree of correlation is smaller than the predetermined value, the biometric authenticity determination unit 3b determines that the predetermined condition is not satisfied.

The biometric authenticity determination unit 3b, among the biological determination spectrums, based on a ratio of a plurality of biometric components, conducts the biometric authenticity determination as to whether the object is the living body. The ratio of a plurality of biometric components is, for example, a ratio between Oxyhemoglobin, HbO2 and Deoxyhemoglobin, Hb. When the ratio of the plurality of biometric components is the predetermined value or above, the biometric authenticity determination unit 3b determines that the predetermined condition is satisfied. Alternatively, when the ratio of the plurality of biometric components is smaller than the predetermined value, the biometric authenticity determination unit 3b determines that the predetermined condition is not satisfied.

When the biometric authenticity determination unit 3b determines that the predetermined condition is satisfied, the biometric authenticity determination unit 3b outputs a fact that the biometric authenticity determination is "true" to the output unit 6. Alternatively, when the biometric authenticity determination unit 3b determines that the predetermined condition is not satisfied, the biometric authenticity determination unit 3b outputs a fact that the biometric authenticity determination is "false" to the output unit 6.

Note that the control unit 3, depending on the area (area selected from area illustrated in FIG. 4B) for acquiring the spectroscopic information, can control a predetermined range that specifies a position of the measuring object 1a of the target installation device 102. For example, the control unit 3, using the display unit for instructing a position to stand to the measuring object, can change the predetermined range. When the seat for sitting the object person to be measured is provided on a stage that can move in an up-and-down direction, a crosswise direction and a front-back direction, the control unit 3 controls the operations of the stage and can adjust the predetermined range.

Next, the biometric determination operation of the living body determination device 10 is specifically described.

FIG. 6 illustrates one procedure of the biometric determination operation. With reference to FIG. 1, FIG. 3 and FIG. 6, the biometric determination operation is described below. Note that, here, as the light irradiation device 101, the white LED is used, as the spectroscopic device 103, the Fourier transform spectrometer is used, and as the image acquisition device 104, the CMOS image sensor is used.

First, at step S100, the image processing unit 3a, in an irradiation state in which the light irradiation device 101 is lighted, controls the spectroscopic operation of the spectroscopic device 103 and acquires, from the image acquisition device 104, the plurality of pieces of image information I1 with respect to the measuring object 1a. Then, the image processing unit 3a, based on the total image information of the plurality of pieces of image information I1, acquires the spectroscopic information and calculates the spectroscopic image information A.

Figure 7:
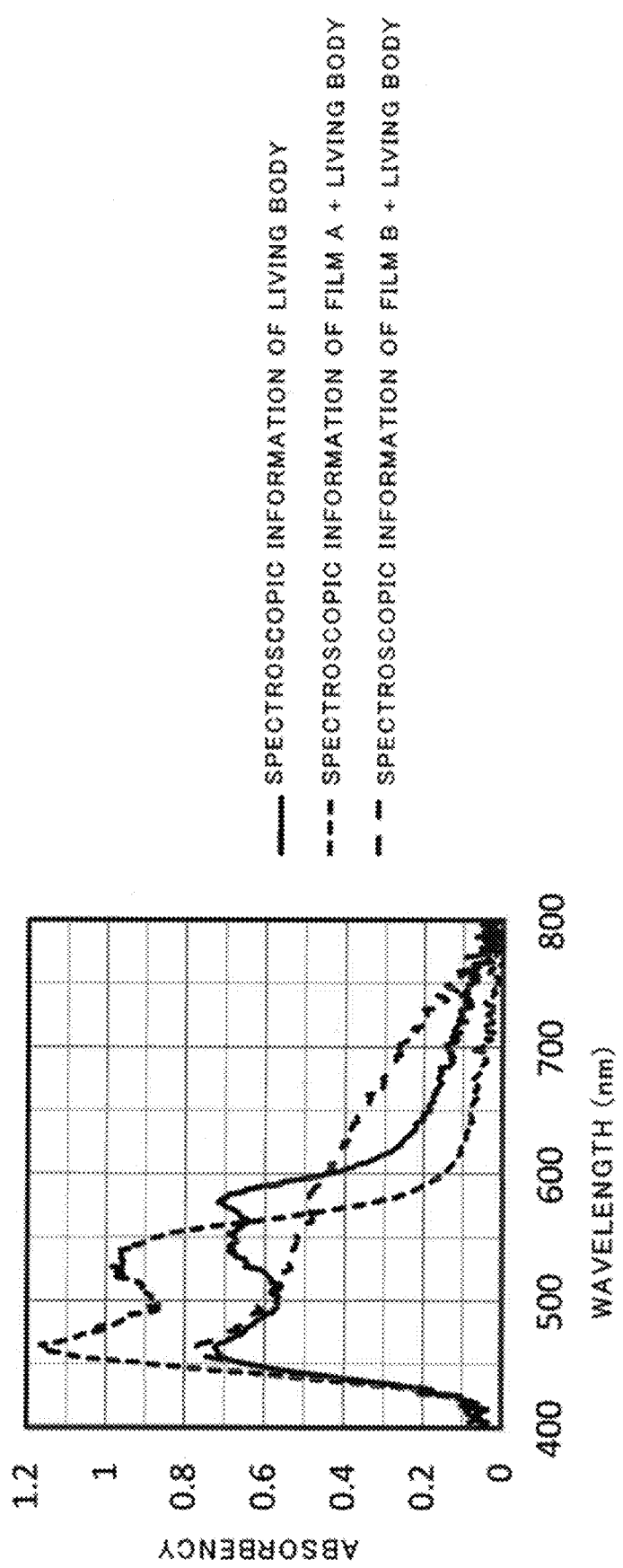
FIG. 7 is a characteristic diagram illustrating one example of a spectrum that is a calculation result of spectroscopic image information.

FIG. 7 illustrates one example of the spectrum that is the calculation result of the spectroscopic image information A. In FIG. 7, a horizontal axis represents the wavelength and a vertical axis represents the absorbency. Measurement examples of the spectroscopic information when the measuring object 1a is each of the "living body" (here cheek r2), "film A+living body," and "film B+living body" are illustrated. Here, the spectroscopic information represents the absorbance spectrum. The "living body" is illustrated with solid lines. The "film A+living body" is when the film A is pasted to the cheek and is illustrated with the broken line with short spaces therebetween. The "film B+living body" is when the film B is pasted to the cheek, and is illustrated with the broken lines with long spaces therebetween. The spectroscopic information of the measuring object 1a includes information of light reflected or scattered at the measuring object 1a, but is mainly derived from the light absorption adjacent to the surface of the measuring object 1a.

Next, at step S101, the biometric authenticity determination unit 3b determines whether the spectrum of the spectroscopic image information A satisfies the predetermined condition. Specifically, the biometric authenticity determination unit 3b determines whether the absorbency of the spectroscopic image information A is higher than the predetermined value, whether the degree of correlation calculated from the spectrum of the spectroscopic image information A and the biological determination spectrum is the predetermined value or above, and whether the ratio of a plurality of components with respect to the living body of the biological determination spectrum is higher than the predetermined value.

Figure 8:
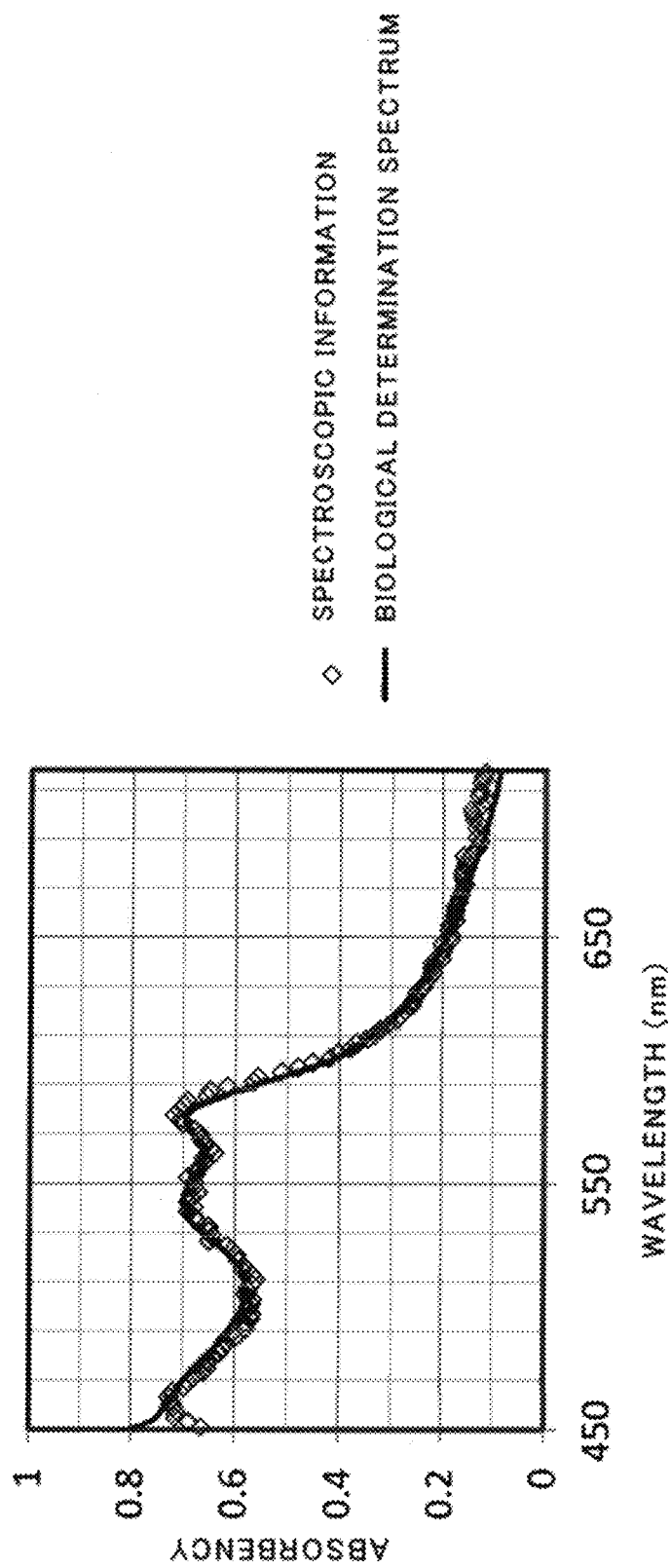
FIG. 8 is a characteristic diagram illustrating a relationship between a reflectance spectrum and a biological determination spectrum when the object is the living body.

FIG. 8 illustrates a relationship between the absorbance spectrum of the spectroscopic image information A of the "living body" and the biological determination spectrum (combination of biometric components). In FIG. 8, a horizontal axis represents the wavelength and a vertical axis represents the absorbency. The "finger alone" is illustrated with argyle marks. The biological determination spectrum is illustrated with the solid lines. Here, the biological determination spectrum is a combination of absorption spectrums (wavelength dependence of extinction coefficient) of the biometric components illustrated in FIG. 5 and can be calculated based on the above described equation 1.

Figure 9:
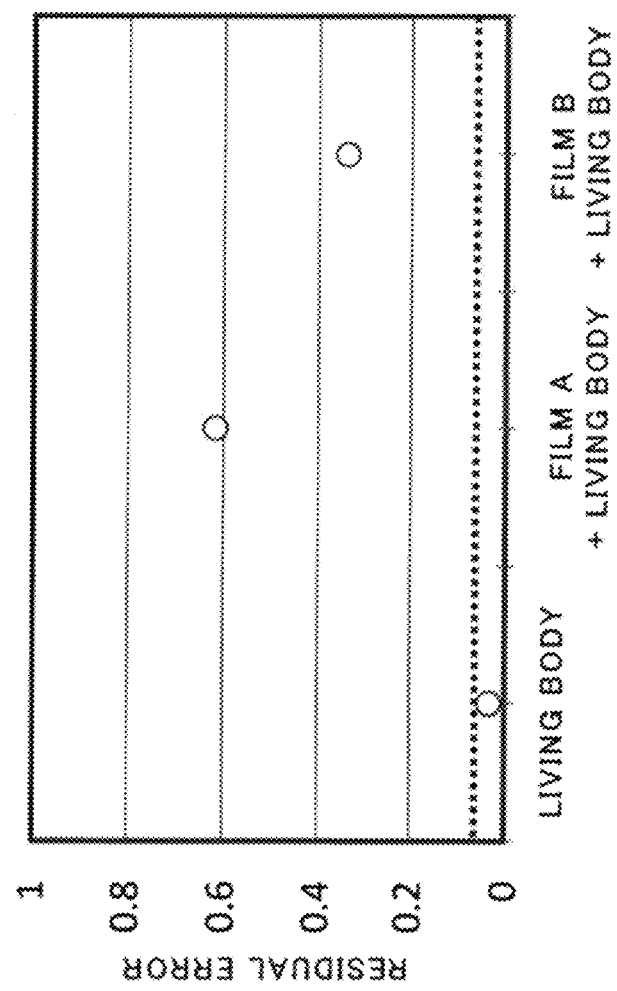
FIG. 9 is a drawing for illustrating a residual error between a reflectance spectrum of each of a living body, film A+living body, and film B+living body and the biological determination spectrum.

FIG. 9 illustrates the residual error between the absorbance spectrum of each of the "living body," "film A+living body," and "film B+living body" of the spectroscopic image information A and the biological determination spectrum. Here, the residual error is the root-mean-square of the difference between the absorbance spectrum and the biological determination spectrum.

The residual error between the reflectance spectrum of the "finger alone" and the biological determination spectrum is a threshold value (for example, 0.08) or below. In this case, the biometric authenticity determination unit 3b determines that degree of correlation between the spectroscopic image information A and the biological determination spectrum is the predetermined value or above. Here, the threshold value is appropriately set depending on a measurement environment and a group of measuring objects.

On the other hand, the residual error between the absorbance spectrum of the "film A+living body" and the biological determination spectrum exceeds the threshold value. In this case, the biometric authenticity determination unit 3b determines that the degree of correlation between the spectroscopic image information A and the biological determination spectrum is smaller than the predetermined value. Similarly, the residual error between the absorbance spectrum of the "film B+living body" and the biological determination spectrum exceeds the threshold value, and thus, the biometric authenticity determination unit 3b determines that the degree of correlation between the spectroscopic image information A and the biological determination spectrum is smaller than the predetermined value.

With respect to the "living body" whose degree of correlation is determined to be equal to or higher than the predetermined value, a determination is also made as to whether a ratio of a plurality of components with respect to the living body of the biological determination spectrum is higher than the predetermined value. In this case, with respect to the coefficient $a_i$, a ratio $a_{HbO2}/a_{Hb}$ between Oxyhemoglobin, HbO2 $a_{HbO2}$ and Deoxyhemoglobin, Hb $a_{Hb}$ is two and is equal or above the threshold value (for example, one). In this case, the biometric authenticity determination unit 3b determines that a ratio of a plurality of components with respect to the living body of the biological determination spectrum is higher than the predetermined value. Here, the threshold value depends on a ratio between a blood volume of a blue pipe and a blood volume of an artery in the group of measuring objects and the measurement site and is appropriately set in accordance with the group of measuring objects and the site.

Note that with respect to whether the absorbency of the spectroscopic image information A is higher than the predetermined value, it is determined that all of "living body," "film A+living body," and "film B+living body" are higher than the threshold value (for example, 0.5 at wavelength 550 nm). The threshold value may be set not only with a specific wavelength, but also with a plurality of wavelengths, and, for example, the absorbency about 550 nm of the biological determination spectrum may be 0.5 or above, and the absorbency about 600 nm may be 0.2 or above.

From above, the biometric authenticity determination unit 3b determines that only the "living body" of the spectroscopic image information A satisfies the predetermined condition.

Similarly, with respect to other areas (for example, jaw r6), the biometric authenticity determination unit 3b determines whether the spectrum of the spectroscopic image information A satisfies the predetermined condition. Specifically, the biometric authenticity determination unit 3b determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

Here, an influence of a substance (cosmetic item or the like) adhered to a face is described. When the cosmetic item (for example, foundation) is applied, by receiving the influence of the cosmetic item, it is possible that the biometric component (Oxyhemoglobin, HbO2 or Deoxyhemoglobin, Hb) may not be detected. The spectroscopic information of the cosmetic ingredient is registered in the memory 4 and when, in the spectroscopic image information A, the biometric component may not be detected and the cosmetic ingredient is detected, different areas (for example, ear r3 or neck r7) are selected and whether the spectroscopic image information A satisfies the predetermined condition is determined. When, in all areas, the biometric component may not be detected and the cosmetic ingredient is detected, a determination is made that the measuring object 1a is not the living body and a fact that the biometric authenticity determination is "false" is output to the output unit 6.

Next, an influence of a skin hair (hair, beard or the like) is described. For example, the beard is growing, and at the cheek r2 and the jaw r7, by receiving the influence of the skin hair, it is possible that the biometric component (Oxyhemoglobin, HbO2 or Deoxyhemoglobin, Hb) may not be detected. When at the cheek r2 and the jaw r7, the biometric component may not be detected and the skin hair is detected, different sites (for example, forehead r1 and neck r7) are selected and whether the spectroscopic image information A satisfies the predetermined condition is determined. The presence or absence of the skin hair can be determined based on the spectrum, and specially can be determined based on the magnitude of the absorbency.

When at step S101, it is determined that the predetermined condition is satisfied, at step S102, the biometric authenticity determination unit 3b determines that the measuring object 1a is the living body and outputs a fact that the biometric authenticity determination is "true" to the output unit 6.

When at step S101, it is determined that the predetermined condition is not satisfied, at step S103, the biometric authenticity determination unit 3b determines that the measuring object 1a is not the living body and outputs a fact that the biometric authenticity determination is "false" to the output unit 6.

The living body determination device 10 according to the present example embodiment uses the spectroscopic image information A, and thus, based on spectrums of one or more areas of the measuring object 1a, can determine whether the object is the living body. Accordingly, compared with the multi-factor authentication system disclosed in PTL 2 which conducts the living body determination based on the diffuse reflectance spectrum from the finger, the fragment of the counterfeit can be detected and by taking into consideration of factors such as cosmetic item and the skin hair other than the skin, the living body can be determined accurately.

Further, it is possible to acquire the spectroscopic image information A reflecting the light absorption adjacent to the surface with respect to any site of the measuring object 1a. As a result, compared with the biological detection device disclosed in PTL 1, a thin counterfeit and tablet terminal can be certainly discriminated.

In the above described living body determination device according to the first example embodiment, the light irradiation device 101 can be referred to as light irradiation means, the spectroscopic device 103 can be referred to as spectroscopic means, and the image acquisition device 104 can be referred to as image acquisition means. The light irradiation means may include a plurality of light irradiation devices respectively.

First application example: biometric authentication device

Next, a biometric authentication device to which the above described living body determination device according to the first example embodiment is applied is described.

The biometric authentication device of this example is obtained by replacing the computing device 105 of the living body determination device 10 illustrated in FIG. 1 with the computing device 105a having the biometric authentication function. Except for the configuration of the computing device 105a, a configuration is basically the same as that of the living body determination device 10.

Figure 10:
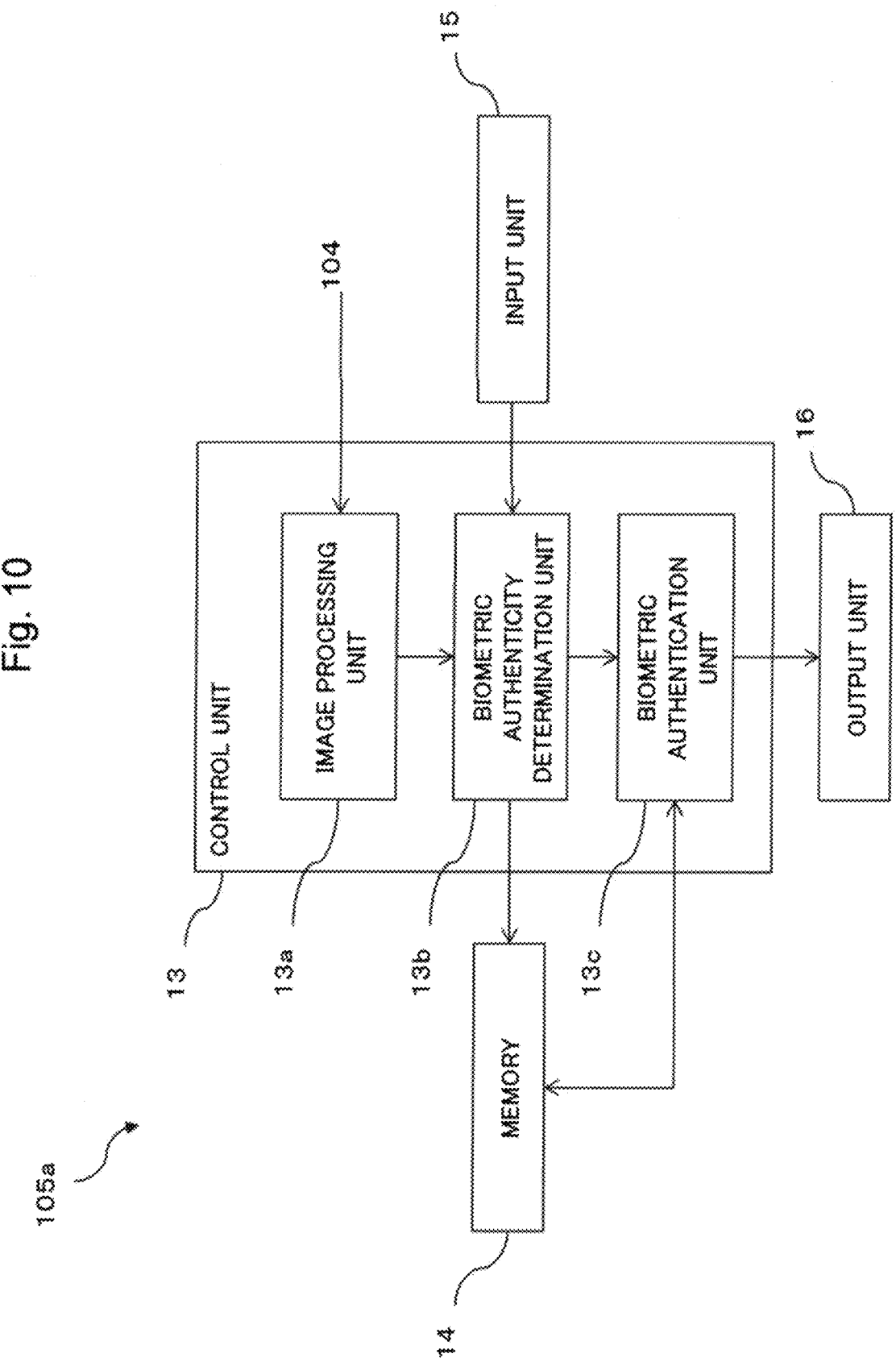
FIG. 10 is a block diagram illustrating a configuration of a computing device of a biometric authentication device that is a first application example in which the living body determination device according to the first example embodiment of the disclosed subject matter is applied.

FIG. 10 is a block diagram illustrating a configuration of the computing device 105a.

Referring to FIG. 10, the computing device 105a includes a control unit 13, a memory 14, an input unit 15 and an output unit 16. The input unit 15 and the output unit 16 are similar to the input unit 5 and the output unit 6 illustrated in FIG. 3.

The memory 14 is similar to the memory 4 illustrated in FIG. 3 and stores the program and data necessary for conducting the biometric authentication (including biometric authentication database). The biometric authentication program can also be provided via the communication network (for example, internet) and the computer-readable recording medium (optical disks such as CD and DVD, USB memory, memory card and the like).

The control unit 13 includes a CPU that operates in accordance with a program, receives an operator guidance from the input unit 15, controls the lighting operation of the light irradiation device 101 and the spectroscopic operation of the spectroscopic device 103, and conducts image processing, a biometric authenticity determination process, and a biometric authentication process. The control unit 13 includes an image processing unit 13a, a biometric authenticity determination unit 13b and a biometric authentication unit 13c.

The biometric authenticity determination unit 13b is the same as the biometric authenticity determination unit 3b illustrated in FIG. 3. The image processing unit 13a has, in addition to the functions of the image processing unit 3a illustrated in FIG. 3, a function of acquiring feature information representing the physical feature. The measuring object 1a is a site representing the physical feature (for example, upper body, cephalic region, face and the like).

The image processing unit 13a controls the lighting operation of the light irradiation device 101. The image processing unit 13a, in an irradiation state in which the light irradiation device 101 is lighted, acquires, from the image acquisition device 105, the plurality of pieces of image information I1 with respect to the measuring object 1a. Then, the image processing unit 13a, using the plurality of pieces of image information I1, calculates the spectroscopic image information A. A calculation operation of the spectroscopic image information A is basically the same as a calculation operation of the spectroscopic image information A of the image processing unit 3a illustrated in FIG. 3. However, although the predetermined areas of the image can be set in advance, the predetermined areas are limited to sites representing the physical features, for example, areas r1 to r7 illustrated in FIG. 4A.

The image processing unit 13a, based on the image information obtained by totaling up (averaging) the plurality of pieces of image information I1, calculates the feature information with respect to the feature point of the measuring object 1a. For example, when the measuring object 1a is the cephalic region, the image processing unit 13a, from the image information, calculates the feature information representing a relative position of parts of a face, a relative size, and features such as shapes of eyes, nose, and jaw. Note that the number of pieces of the image information I1 used for the calculation of the feature information is not specially limited.

When the biometric authenticity determination unit 13b determines that the measuring object 1a is the living body, the biometric authentication unit 13c acquires, from the memory 14, information necessary for the biometric authentication (biometric authentication information) and compares the biometric authentication information with the feature information. For example, when the biometric authentication is conducted using the face, the feature information of the face registered in advance as the biometric authentication information is stored in the memory 14 in advance. The biometric authentication unit 13c acquires, from the memory 14, the feature information and compares the authentication information with the feature information.

When the feature information matches with the authentication information, the biometric authentication unit 13c determines that a person is an authorized person and outputs information representing that the authentication is successful to the output unit 16.

Alternatively, when the feature information does not match with the authentication information, the biometric authentication unit 13c determines that a person is an unauthorized person and outputs information representing an authentication error to the output unit 16. Further, also when the biometric authenticity determination unit 13b determines that the measuring object 1a is not the living body, the biometric authentication unit 13c outputs information representing the authentication error to the output unit 16.

Next, the biometric authentication operation of the biometric authentication device of this example is specifically described.

Figure 11:
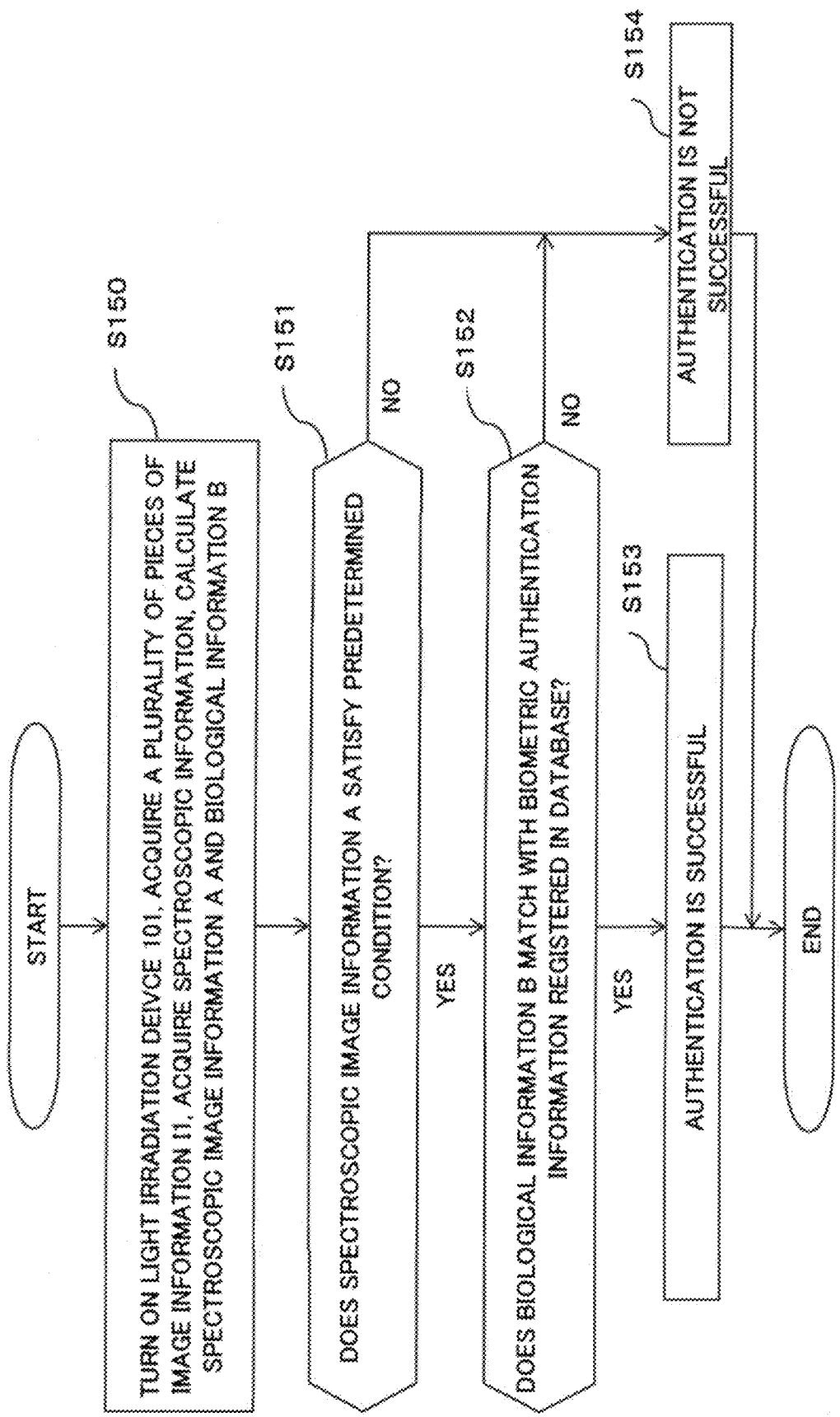
FIG. 11 is a flowchart illustrating one procedure of a biometric authentication operation of a biometric authentication device of the first application example.

FIG. 11 illustrates one procedure of the biometric authentication operation. With reference to FIG. 10 and FIG. 11, the biometric authentication operation is described below. Note that here, as the light irradiation device 101, the white LED is used, as the spectroscopic device 103, the Fourier transform spectrometer is used, and as the image acquisition device 104, the CMOS image sensor is used.

First, at step S150, the image processing unit 13a, in an irradiation state in which the light irradiation device 101 is lighted, controls the spectroscopic operation of the spectroscopic device 103 and acquires, from the image acquisition device 104, the plurality of pieces of image information I1 with respect to the measuring object 1a. Then, the image processing unit 13a, from the total image information of the plurality of pieces of image information I1, acquires the spectroscopic information, calculates the spectroscopic image information A, and from the plurality of pieces of image information I1, calculates the feature information.

At step S151, the biometric authenticity determination unit 13b determines whether the spectrum of the spectroscopic image information A satisfies the predetermined condition. Specifically, the biometric authenticity determination unit 13b determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

When the answer to the determination at step S151 is "Yes," at step S152, the biometric authentication unit 13c acquires, from the memory 14, the biometric authentication information and determines whether the feature information matches with the biometric authentication information.

When the feature information matches with the biometric authentication information, at step S153, the biometric authentication unit 13c determines that a person is an authorized person and outputs information representing that the authentication is successful to the output unit 16.

Alternatively, when an answer to the determination at step S151 or step S152 is "No," at step S154, the biometric authentication unit 13c determines that a person is not an authorized person, and outputs information representing the authentication error to the output unit 16.

According to the biometric authentication device of this example, based on the extremely accurate living body determination in which the counterfeit is difficult, the biometric authentication is conducted to the site that is determined to be the living body, and thus, the reliability of the biometric authentication can be improved and the advanced security can be ensured.

Further, since the living body determination device 10 and the biometric authentication device of this example share the light irradiation device 101, the spectroscopic device 104 and the image acquisition device 105, the upsizing of devices can be suppressed.

Note that pieces of biometric authentication information may be accumulated in an external storage device (database) or a database server. In this case, the biometric authentication unit 13c is, via an unillustrated network, coupled to the external storage device (database) or a database server.

Although the biometric authentication information is registered in the database, it is not limited to this. The biometric authentication information may be stored in storage means such as an IC (Integrated Circuit) tag. For example, if the IC tag storing the biometric authentication information is mounted to a passport or the like, when the passport is presented, from the IC tag, the biometric authentication information is red, and the biometric authentication information is collated with the feature information.

Further, the image processing unit 13a, from among the plurality of pieces of image information I1, may select image information of a wavelength band in which the feature information is easily acquired. For example, the image processing unit 13a, among the plurality of pieces of image information I1, may remove image information of a side of a long wavelength and may select image information of a side of a short wavelength.

Second Example Embodiment

Figure 12:
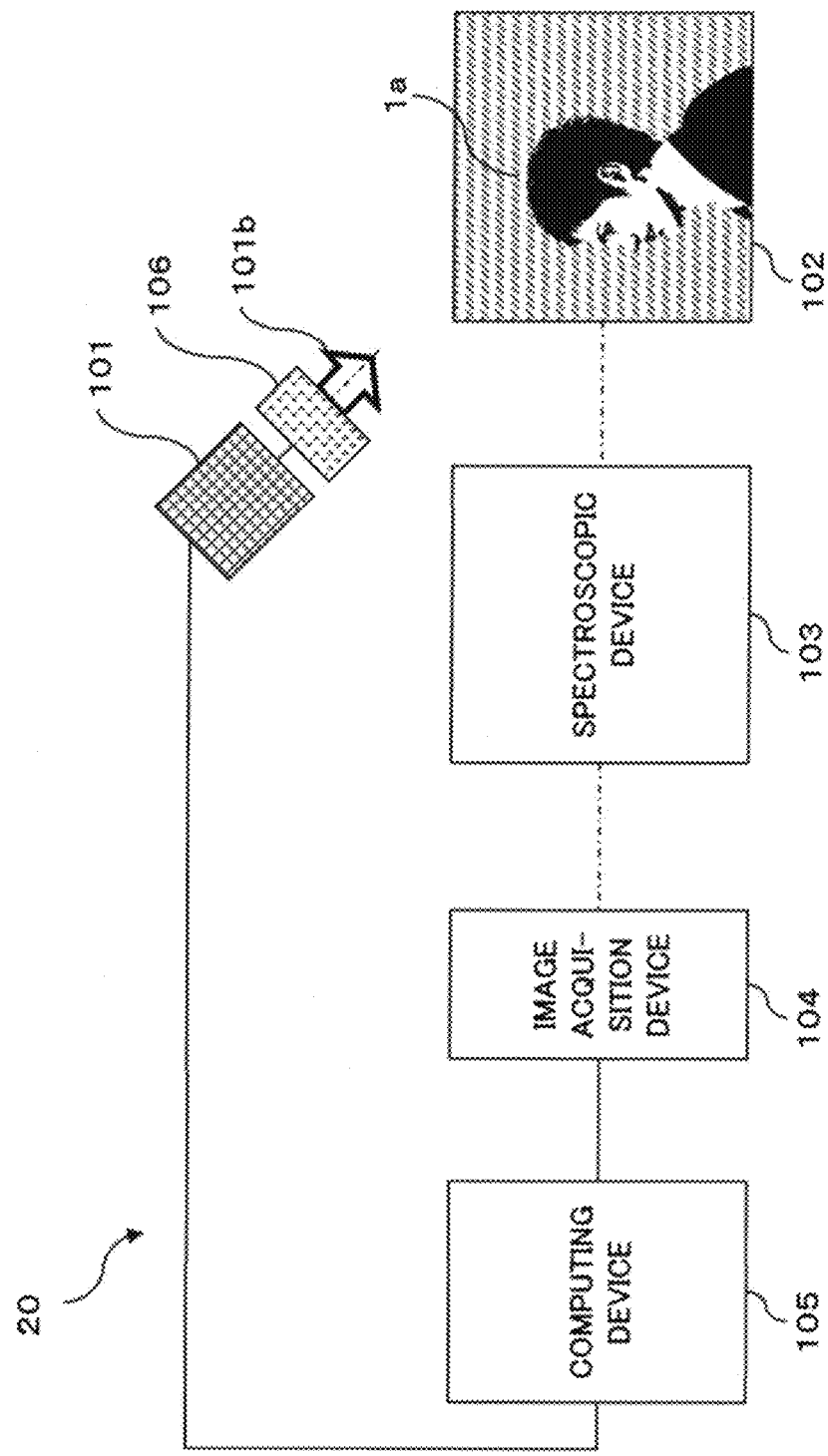
FIG. 12 is a block diagram illustrating a configuration of a living body determination device according to a second example embodiment of the disclosed subject matter.

FIG. 12 is a block diagram illustrating a configuration of the living body determination device according to the second example embodiment of the disclosed subject matter.

Although the living body determination device according to the second example embodiment of the disclosed subject matter has a configuration similar to that of the device of the first example embodiment, the living body determination device according to the second example embodiment of the disclosed subject matter further includes an irradiation position control device for the light irradiation device. Here, a configuration different from that of the first example embodiment is mainly described, and descriptions of the same configurations are omitted.

An irradiation position control device 106 is a device for limiting an irradiate range of light 101b only to an area for comparing the spectrum with the biological determination spectrum. As the irradiation position control device 106, for example, a liquid crystal shutter, a DMD (digital mirror device and the like can be used.

The liquid crystal shutter is a device that, by applying voltage to liquid crystals sandwiched between polarizing plates, controls the transmission or blocking of light. A plurality of areas in which electrodes are arranged are provided, and for each area, by controlling the voltage, the area in which the light transmits can be controlled arbitrarily.

The DMD is obtained by arranging movable micromirrors in a grid pattern. By changing the tilt of the mirror with the voltage, ON and OFF can be switched, and a mirror area assumed to be ON can be controlled arbitrarily.

Next, a biometric determination operation of the living body determination device according to the present example embodiment is specifically described.

Figure 13:
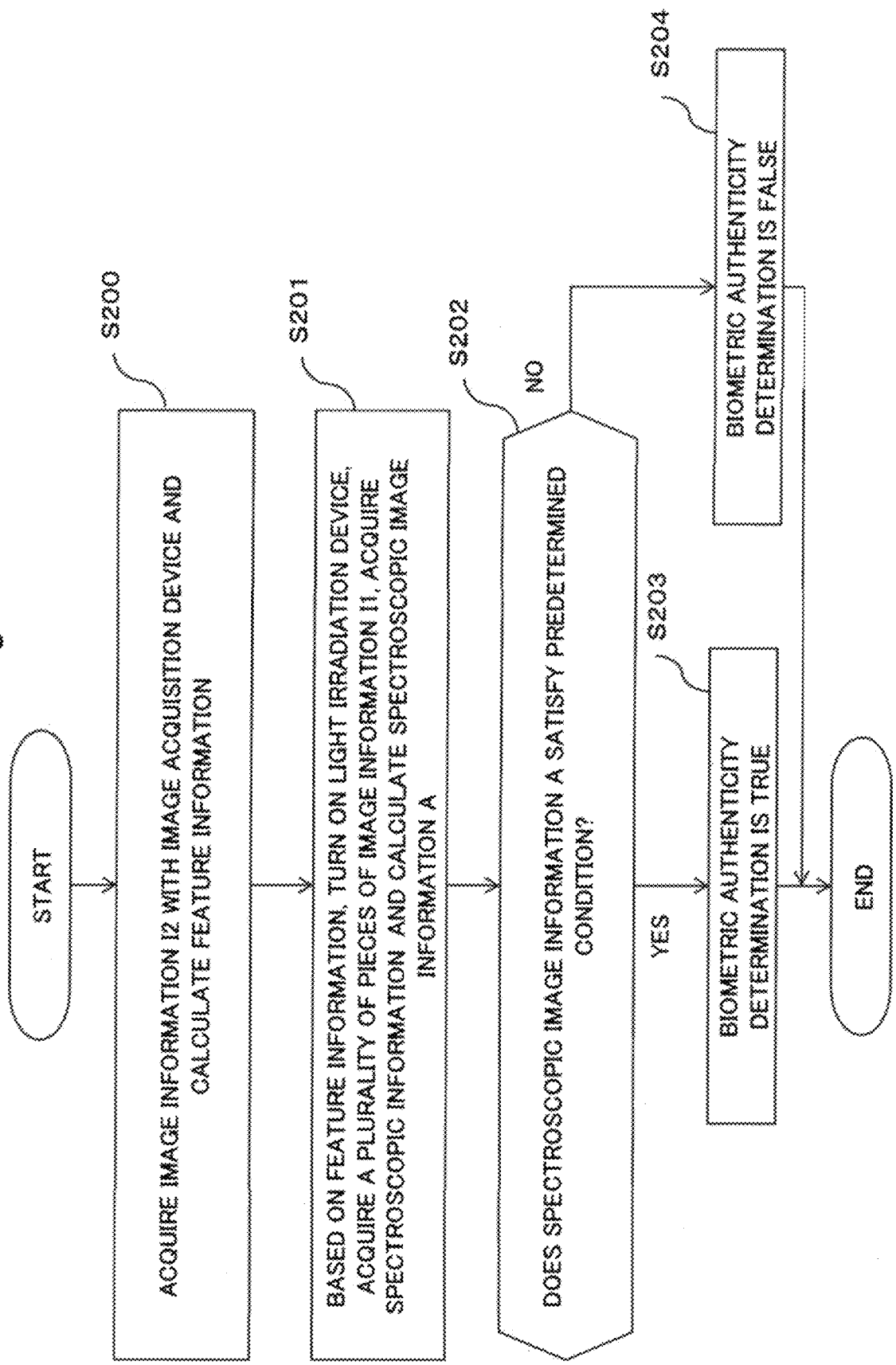
FIG. 13 is a flowchart illustrating one procedure of a biometric determination operation of the living body determination device illustrated in FIG. 12.

FIG. 13 illustrates one procedure of the biometric determination operation. With reference to FIG. 3, FIG. 12 and FIG. 13, the biometric determination operation is described below.

First, at step S200, the image processing unit 3a acquires, from the image acquisition device 104, image information I2 with respect to the measuring object 1a and, from the image information I2, calculates the feature information. Here, if the feature information can be calculated, the light irradiation device 101 does not need to be lighted. When the feature information may not be calculated, the control unit 3 causes the light irradiation device 101 to be lighted, and the image processing unit 3a acquires the image information I2 and, from the image information I2, calculates the feature information.

Next, at step S201, the control unit 3 causes the light irradiation device 101 to be lighted, controls the irradiation position control device 106 such that based on the feature information, only specific areas (r1 to r7) are irradiated with light and controls the spectroscopic operation of the spectroscopic device 103. Then, the image processing unit 3a acquires, from the image acquisition device 104, the plurality of pieces of image information I1 with respect to the measuring object 1a, based on the total image information of the plurality of pieces of image information I1, acquires the spectroscopic information and calculates the spectroscopic image information A.

Next, at step S202, the biometric authenticity determination unit 3b determines whether the spectrum of the spectroscopic image information A satisfies the predetermined condition. Specifically, the biometric authenticity determination unit 3b determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

At step S202, when it is determined that the predetermined condition is satisfied, at step S203, the biometric authenticity determination unit 3b determines that the measuring object 1a is the living body and outputs a fact that the biometric authenticity determination is "true" to the output unit 6.

Alternatively, when at step S202, it is determined that the predetermined condition is not satisfied, at step S204, the biometric authenticity determination unit 3b determines that the measuring object 1a is not the living body and outputs a fact that the biometric authenticity determination is "false" to the output unit 6.

Here, the brightness of the light irradiation device 101 is controlled such that the glare is suppressed for the object person to be measured. The glare is evaluated depending on, for example, a glare index. A glare contrast g of individual light sources is represented by the equation 2, and the entire glare index GI is represented with the equation 3.

[Mathematical 2]

$$g = 0.478 \frac{L_s^{1.6} \omega^{0.8}}{F \times p^{1.6}} \quad \text{Equation 2}$$

[Mathematical 3]

$$GI = 10\log_{10} 0.5 \sum g \quad \text{Equation 3}$$

Here, the $L_s$ represents the luminance of the light source, $\omega$ represents the solid angle of the light source as viewed from an observer, p represents a position index, and F represents the average luminance of the field of view. The control unit 3 controls the brightness of the light irradiation device 101 such that the GI is 21 or less, and preferably the GI is 18 or less.

According to the living body determination device of the present example embodiment, in addition to effects described in the first example embodiment, it is possible to reduce the glare, reduce a load of a person to be authenticated, and improve the operability of the living body determination device.

The variation described in the first example embodiment can also be applied to the living body determination device according to the present example embodiment.

Second application example: biometric authentication device

Next, a biometric authentication device to which the above described living body determination device according to the second example embodiment is applied is described.

Although the biometric authentication device of this example has the same configuration as that of the above described biometric authentication device that is the first application example, the biometric authentication device of this example uses an irradiation position control device for a light irradiation device and includes a computing device 105b having an irradiation position control unit instead of the computing device 105.

Figure 14:
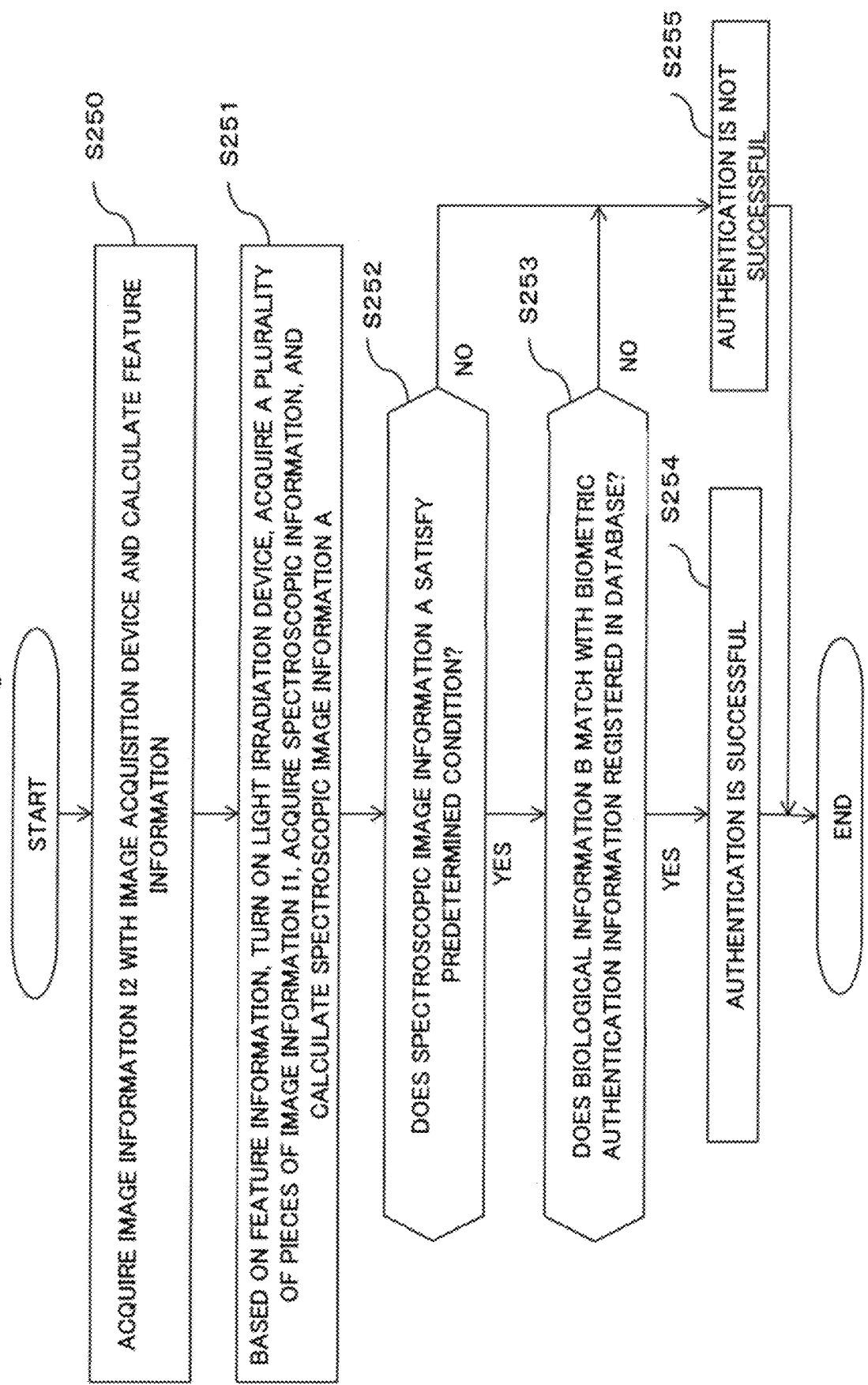
FIG. 14 is a flowchart illustrating one procedure of a biometric authentication operation of a biometric authentication device that is a second application example in which the living body determination device according to the second example embodiment of the disclosed subject matter is applied.

FIG. 14 illustrates one procedure of the biometric authentication operation.

First, at step S250, the image processing unit 13a acquires, from the image acquisition device 104, the image information I2 with respect to the measuring object 1a, and from the image information I2, calculates the feature information. Here, if the feature information can be calculated, the light irradiation device 101 does not need to be lighted. When the feature information may not be calculated, the control unit 13 causes the light irradiation device 101 to be lighted and the image processing unit 13a acquires the image information I2 and, from the image information I2, calculates the feature information.

Next, at step S251, the control unit 13 causes the light irradiation device 101 to be lighted, controls the irradiation position control device 106 such that based on the feature information, only the specific areas (r1 to r7) are irradiated with the light, and controls the spectroscopic operation of the spectroscopic device 103. Then, the image processing unit 13a, from the image acquisition device 104, acquires the plurality of pieces of image information I1 with respect to the measuring object 1a, based on the total image information of the plurality of pieces of image information I1, acquires the spectroscopic information, and calculates the spectroscopic image information A.

Next, at step S252, the biometric authenticity determination unit 13b determines whether the spectrum of the spectroscopic image information A satisfies the predetermined condition. Specifically, the biometric authenticity determination unit 13b determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

When the answer to the determination at step S252 is "Yes," at step S253, the biometric authentication unit 13c acquires, from the memory 14, the biometric authentication information and determines whether the feature information matches with the biometric authentication information. When the feature information matches with the biometric authentication information, at step S254, the biometric authentication unit 13c determines that a person is the authorized person and outputs information representing that the authentication is successful to the output unit 16.

When the answer to the determination at step S252 or step S253 is "No," at step S255, the biometric authentication unit 13c determines that a person is not an authorized person and outputs information representing the authentication error to the output unit 16.

Note that, in the above described biometric authentication operation, the order of step S252 and step S253 may be changed.

According to the biometric authentication device of this example, in addition to the effects described in the first application example, it is possible to reduce the glare, reduce the load of a person to be authenticated, and improve the operability of the living body determination device.

Also to the biometric authentication device of this example, a configuration and a variation described in the first application example can be applied.

Third Example Embodiment

Figure 15:
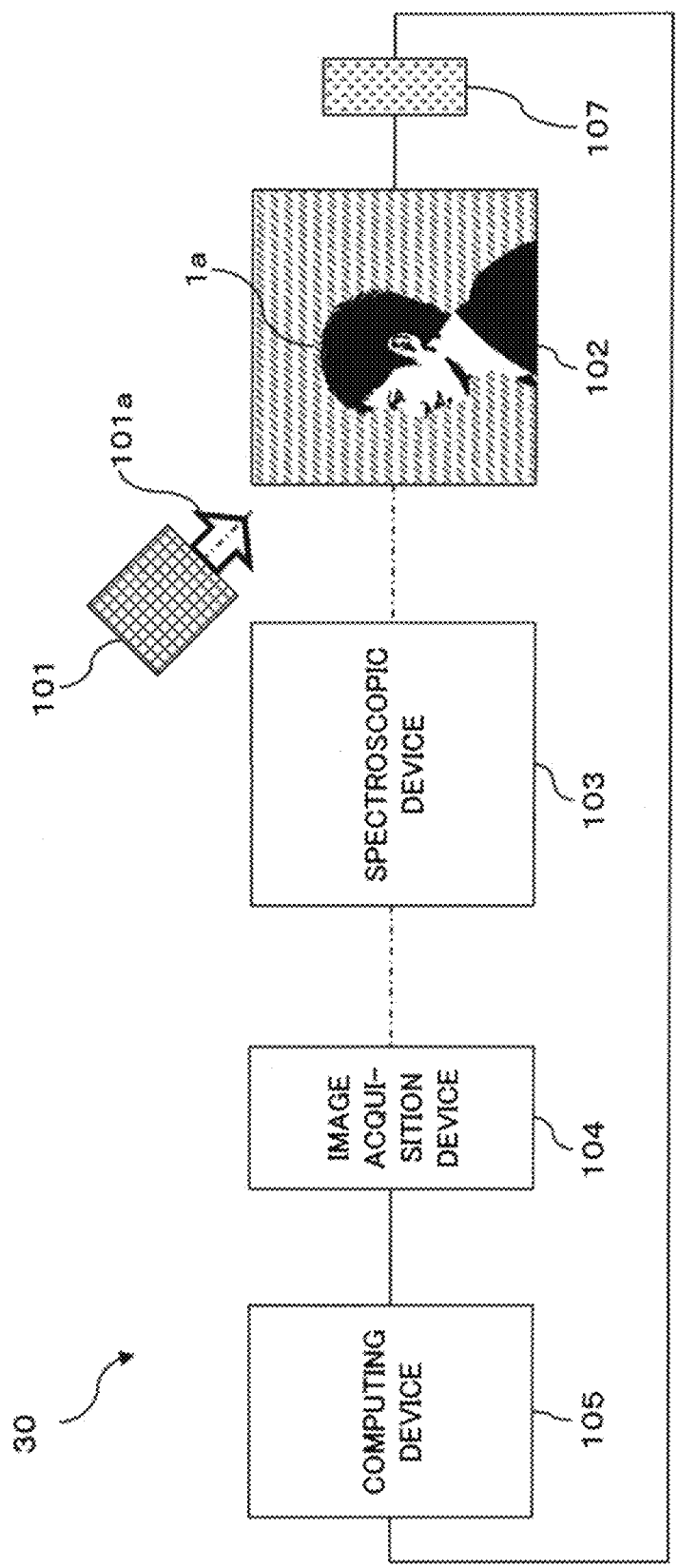
FIG. 15 is a block diagram illustrating a configuration of a living body determination device according to a third example embodiment of the disclosed subject matter.

FIG. 15 is a block diagram illustrating a configuration of the living body determination device according to the third example embodiment of the disclosed subject matter.

Referring to FIG. 15, a living body determination device 30 includes a light irradiation device 101, a target installation device 102, a spectroscopic device 103, an image acquisition device 104, a computing device 105, and a target position control device 107. The target installation device 102, the spectroscopic device 103, the image acquisition device 104, and the computing device 105 are the same as the devices described in the first example embodiment. A configuration different from that of the first example embodiment is mainly described below, and descriptions of the same configuration are omitted.

The target position control device 107, based on the feature information that is acquired and calculated by the image processing unit 3a, induces the position of the measuring object 1a in the specific range. Induction methods include a method of making the instruction using the display, a method of making the instruction using the speaker, and a method of moving the target installation device 102.

Next, the biometric determination operation of the living body determination device according to the present example embodiment is specifically described.

Figure 16:
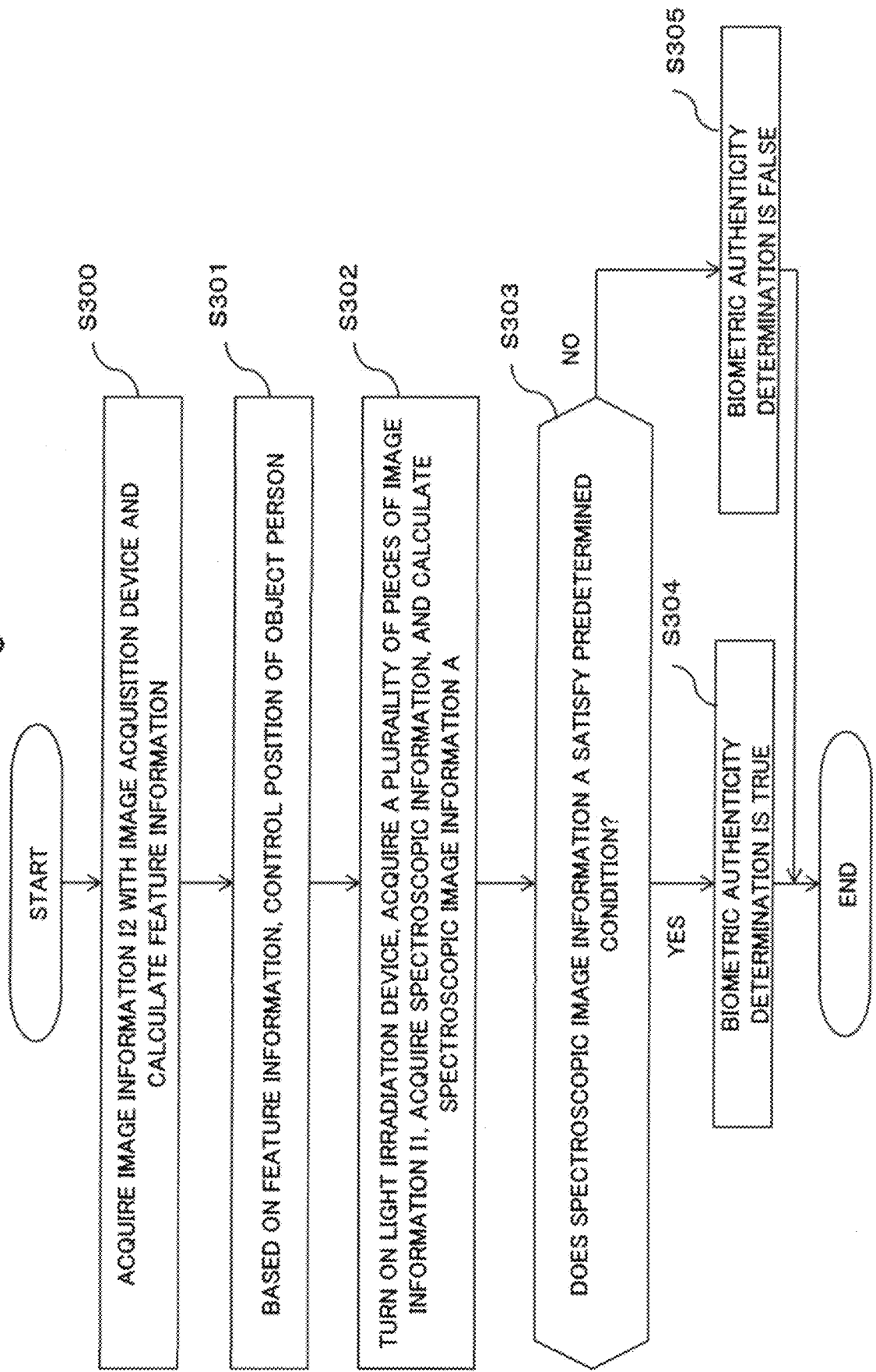
FIG. 16 is a flowchart illustrating one procedure of a biometric determination operation of a living body determination device illustrated in FIG. 15.

FIG. 16 illustrates one procedure of the biometric determination operation. With reference to FIG. 3, FIG. 15 and FIG. 16, the biometric determination operation is described below.

First, at step S300, the image processing unit 3a acquires, from the image acquisition device 104, the image information I2 with respect to the measuring object 1a, and calculates, from the image information I2, the feature information. Here, if the feature information can be calculated, the light irradiation device 101 does not need to be lighted. If the feature information may not be calculated, the control unit 3 causes the light irradiation device 101 to be lighted and the image processing unit 3a acquires the image information I2 and, from the image information I2, calculates the feature information.

Next, at step S301, the control unit 3, based on the feature information, causes the target position control device 107 to be operated and moves the measuring object 1a in the predetermined areas. Specially, the control unit 3 controls the target position control device 107 such that only the specific areas (r1 to r7) are irradiated with light.

At step S302, the image processing unit 3a causes the light irradiation device 101 to be lighted and controls the spectroscopic operation of the spectroscopic device 103. Then, the image processing unit 3a acquires, form the image acquisition device 104, the plurality of pieces of image information I1 with respect to the measuring object 1a, based on the total image information of the plurality of pieces of image information I1, acquires the spectroscopic information and calculates the spectroscopic image information A.

Next, at step S303, the biometric authenticity determination unit 3b determines whether the spectrum of the spectroscopic image information A satisfies the predetermined condition. Specifically, the biometric authenticity determination unit 3b determines whether the absorbency of the spectroscopic image information A is the predetermined value or above, whether the degree of correlation calculated from the spectrum of the spectroscopic image information A and the biological determination spectrum is the predetermined value or above, and whether a ratio of a plurality of components with respect to the living body of the biological determination spectrum is the predetermined value or above.

At step S303, when it is determined that the predetermined condition is satisfied, at step S304, the biometric authenticity determination unit 3b determines that the measuring object 1a is the living body and outputs a fact that the biometric authenticity determination is "true" to the output unit 6.

Alternatively, when at step S303, it is determined that the predetermined condition is not satisfied, at step S305, the biometric authenticity determination unit 3b determines that the measuring object 1a is not the living body and outputs a fact that the biometric authenticity determination is "false" to the output unit 6.

According to the living body determination device of the present example embodiment, in addition to the effects described in the first example embodiment, it is possible to reduce the glare, reduce a load of a person to be authenticated, and improve the operability of the living body determination device.

Figure 17:
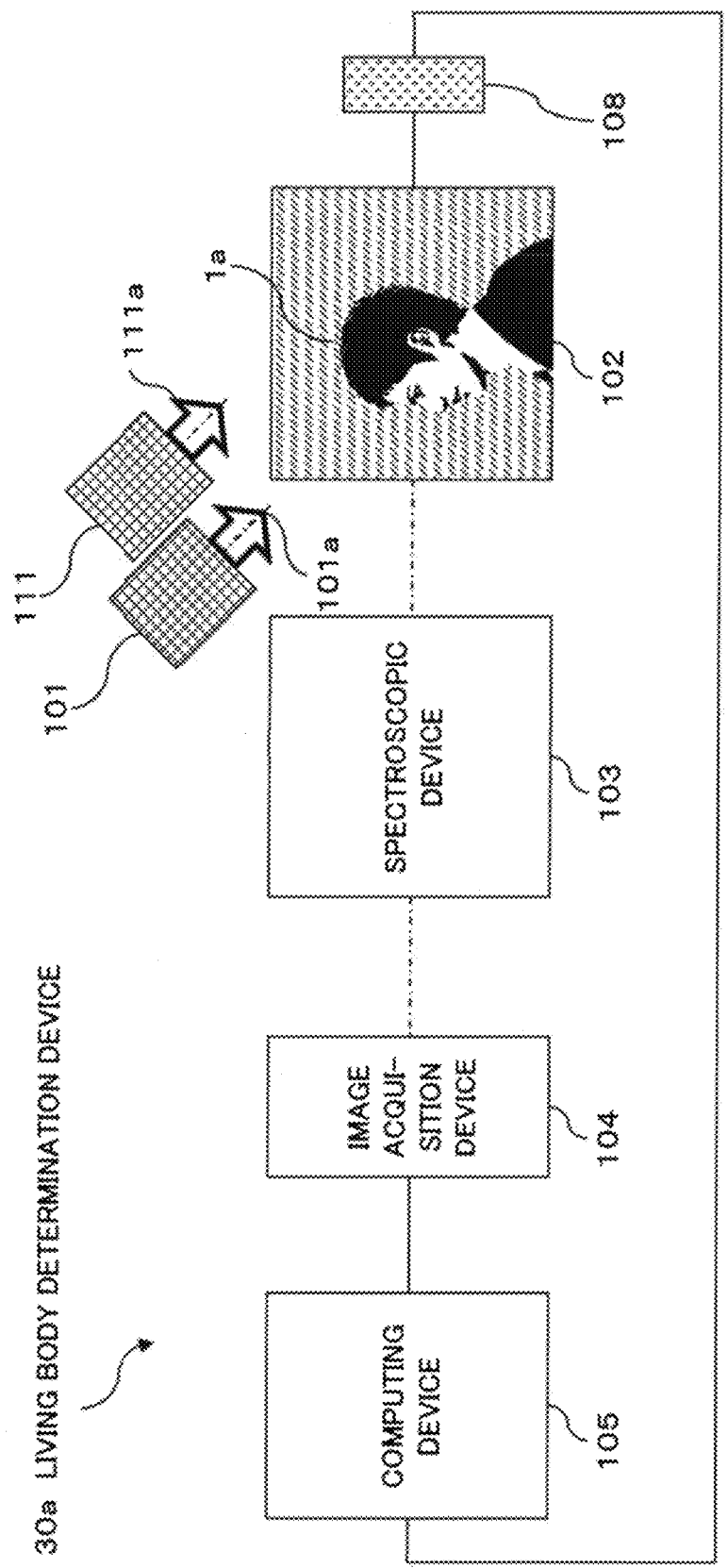
FIG. 17 is a block diagram illustrating a configuration of a first variation of a living body determination device according to a third example embodiment of the disclosed subject matter.
Figure 18:
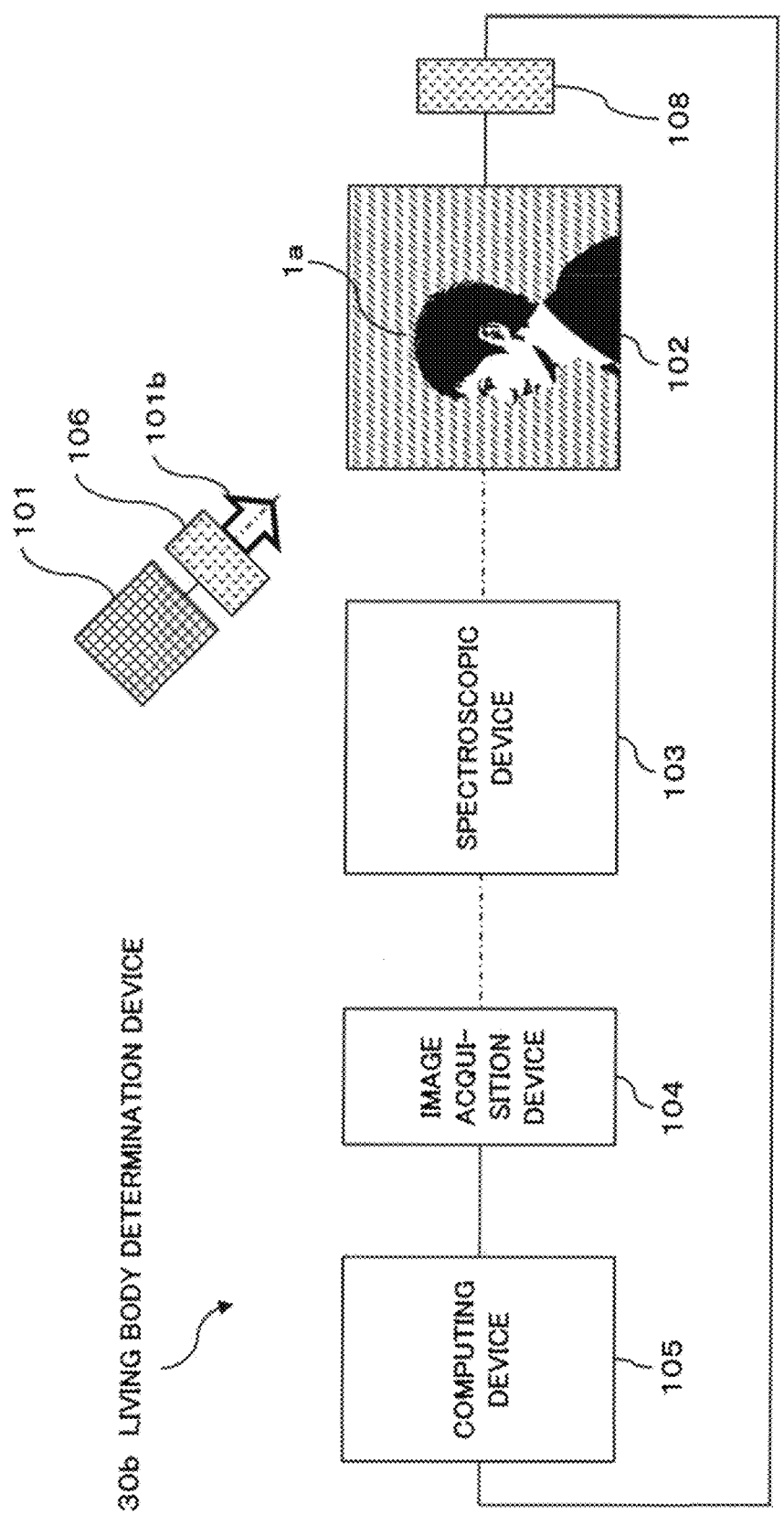
FIG. 18 is a block diagram illustrating a configuration of a second variation of a living body determination device according to the third example embodiment of the disclosed subject matter.

Also to the living body determination device according to the present example embodiment, the variation described in the first example embodiment can be applied. The variation of living body determination device according to the present example embodiment is described with reference to FIG. 17 and FIG. 18. FIG. 17 is a block diagram illustrating a configuration of the first variation of the living body determination device according to the third example embodiment of the disclosed subject matter. FIG. 18 is a block diagram illustrating a configuration of the second variation of the living body determination device according to the third example embodiment of the disclosed subject matter.

The living body determination device 30a illustrated in FIG. 17 has the same configuration as that of the living body determination device 30 according to the third example embodiment of the disclosed subject matter and further includes a light irradiation device 111. Although the light irradiation device 111 has the same function as that of the light irradiation device 101, the light irradiation device 111 irradiates an area with light 111a which area is different from the irradiation position of the light irradiation device 101 relative to the measuring object 1a.

According to the living body determination device 30a, in addition to the effects described in the first example embodiment, it is possible to reduce the glare, recue the load of a person to be authenticated, simultaneously conduct the living body determination of a plurality of positions to shorten the measurement time, and improve the operability of the living body determination device.

The living body determination device 30b illustrated in FIG. 18 has the same configuration as that of the living body determination device 30 according to the third example embodiment of the disclosed subject matter and further includes the irradiation position control device 106. The irradiation position control device 106 is the same as the device described in the second example embodiment.

According to the living body determination device 30b, in addition to the effects described in the first example embodiment, it is possible to reduce the glare, reduce the load of a person to be authenticated, simultaneously conduct the living body determination of a plurality of positions to shorten the measurement time, and improve the operability of the living body determination device.

Third application example: biometric authentication device

Next, a biometric authentication device to which the above described living body determination device according to the third example embodiment is applied is described.

Figure 19:
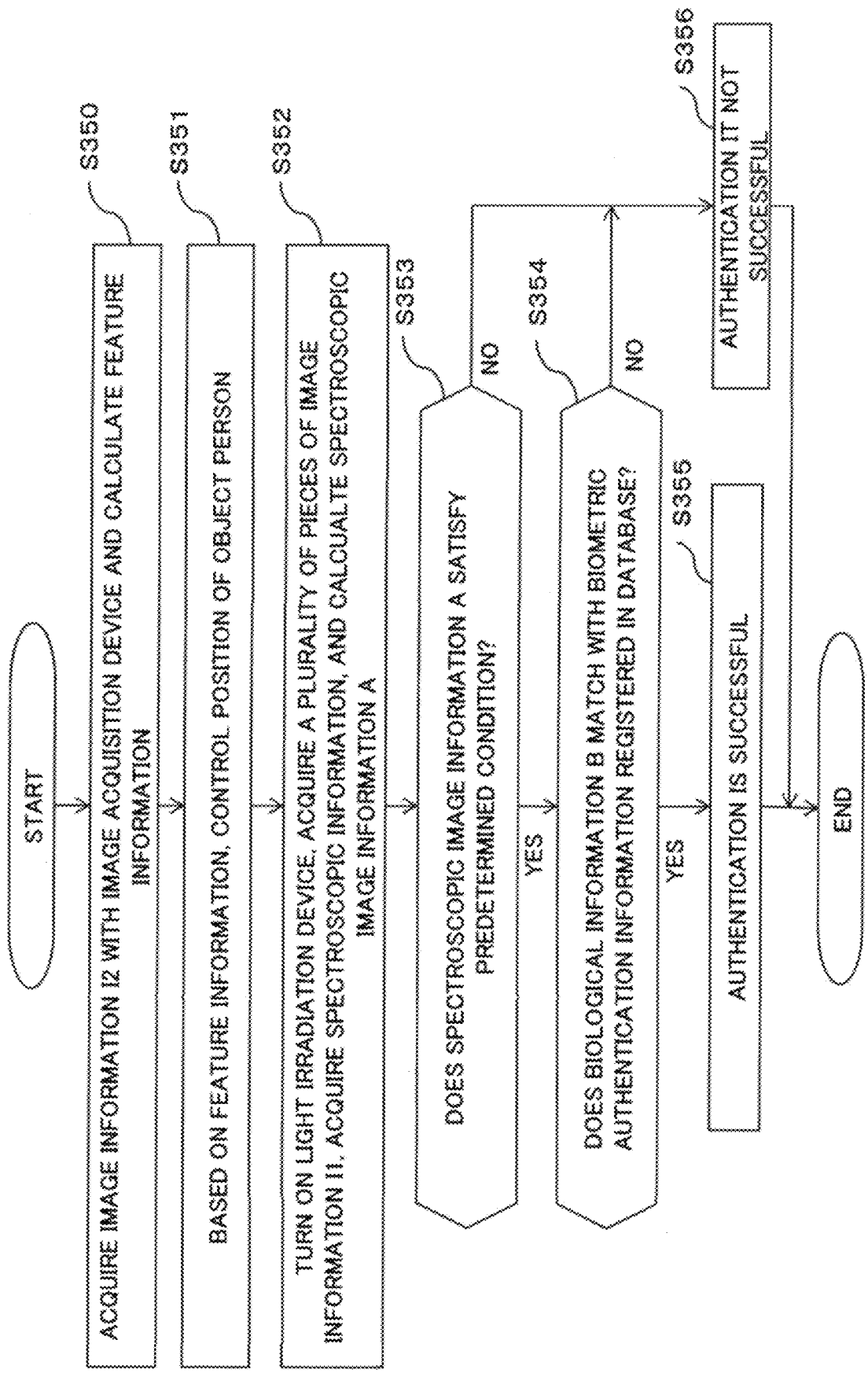
FIG. 19 is a flowchart illustrating one procedure of a biometric authentication operation of a biometric authentication device that is a third application example in which the living body determination device according to the third example embodiment of the disclosed subject matter is applied.

The computing device 105 of the biometric authentication device of this example also has a configuration illustrated in FIG. 10. FIG. 19 illustrates one procedure of the biometric authentication operation.

First, at step S350, the image processing unit 13a acquires, from the image acquisition device 104, the image information I2 with respect to the measuring object 1a and, from the image information I2, calculates the feature information. Here, if the feature information can be calculated, the light irradiation device 101 does not need to be lighted. Alternatively, when the feature information may not be calculated, the control unit 13 causes the light irradiation device 101 to be lighted and the image processing unit 13a acquires the image information I2 and, from the image information I2, calculates the feature information.

Next, at step S351, the control unit 13, based on the feature information, operates the target position control device 107 and moves the measuring object 1a in the predetermined areas. Specially, the control unit 13 controls the target position control device 107 such that only the specific areas (r1 to r7) are irradiated with light.

At step S352, the control unit 13 causes the light irradiation device 101 to be lighted and controls the spectroscopic operation of the spectroscopic device 103. Then, the image processing unit 13a, from the image acquisition device 104, acquires the plurality of pieces of image information I1 with respect to the measuring object 1a, based on the total image information of the plurality of pieces of image information I1, acquires the spectroscopic information, and calculates the spectroscopic image information A.

Next, at step S353, the biometric authenticity determination unit 13b determines whether the spectrum of the spectroscopic image information A satisfies the predetermined condition. Specifically, the biometric authenticity determination unit 13b determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

When the answer to the determination at step S353 is "Yes," at step S354, the biometric authentication unit 13c acquires, from the memory 14, the biometric authentication information and determines whether the feature information matches with the biometric authentication information. When the feature information matches with the biometric authentication information, at step S355, the biometric authentication unit 13c determines that a person is an authorized person and outputs information representing that the authentication is successful to the output unit 16.

When the answer to the determinations at step S353 or step S354 is "No," at step S356, the biometric authentication unit 13c determines that a person is not an authorized person and outputs information representing the authentication error to the output unit 16.

Note that, in the above described biometric authentication operation, the order of step S353 and step S354 may be changed.

According to the biometric authentication device of this example, in addition to the effects described in the first application example, it is possible to reduce the glare, reduce the load of a person to be authenticated, and improve the operability of the living body determination device.

To the biometric authentication device of this example also, a configuration and a variation described in the first application example can be applied.

Fourth Example Embodiment

Figure 20:
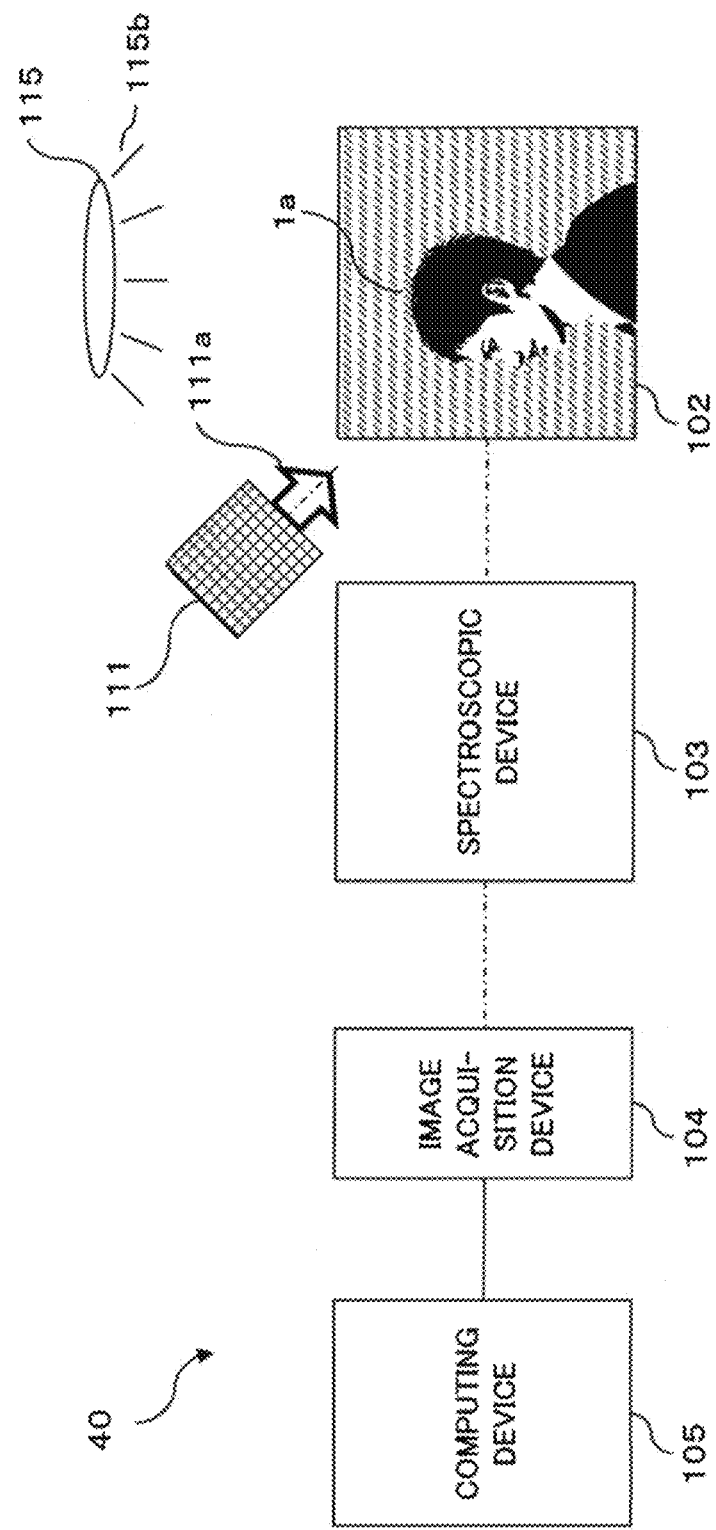
FIG. 20 is a block diagram illustrating a configuration of a living body determination device according to a fourth example embodiment of the disclosed subject matter.

FIG. 20 is a block diagram illustrating a configuration of the living body determination device according to the fourth example embodiment of the disclosed subject matter.

Referring to FIG. 20, a living body determination device 40 includes a light irradiation device 111, a target installation device 102, a spectroscopic device 103, an image acquisition device 104, and a computing device 105. The target installation device 102, the spectroscopic device 103, the image acquisition device 104, and the computing device 105 are the same as the devices described in the first example embodiment. A configuration different from that of the first example embodiment is mainly described below, and descriptions of the same configuration are omitted.

Figure 21:
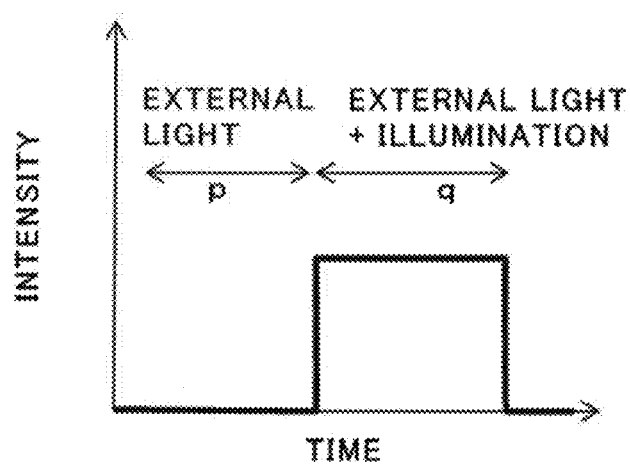
FIG. 21 is a drawing for explaining operations of a light irradiation device of the living body determination device illustrated in FIG. 20.

The light irradiation device 111 irradiates the target installation device 102 with the light 111a. FIG. 21 illustrates an operation example of the light irradiation device 111. At an interval p, the light irradiation device 111 is turned off. At this time, the measuring object 1a is irradiated with external light 115b from an external light source 115. At an interval q, the light irradiation device 111 is lighted. At this time, the measuring object 1a is irradiated with the light 111a and the external light 115b. The light irradiation device 111 is positioned to irradiate the measuring object 1a from the front. When the target installation device 102 is viewed from the vertical direction, the optical axis of the light irradiation device 111 and the optical axis of the spectroscopic device 103 cross at an angle θ. The angle θ can be appropriately set, but is preferably less than 90 degrees.

Next, the biometric determination operation of the living body determination device according to the present example embodiment is specifically described.

Figure 22:
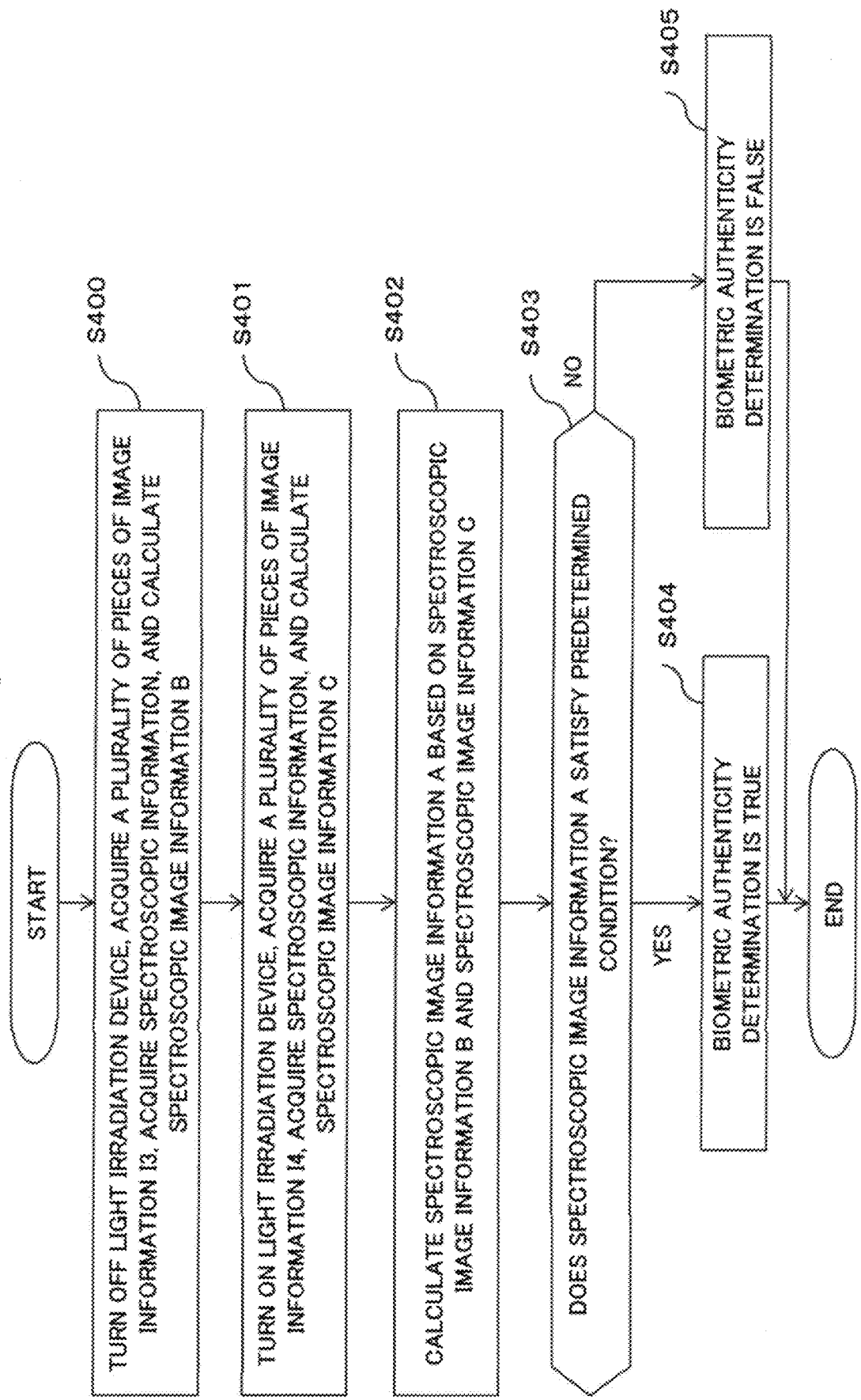
FIG. 22 is a flowchart illustrating one procedure of a biometric determination operation of the living body determination device illustrated in FIG. 20.

FIG. 22 illustrates one procedure of the biometric determination operation. With reference to FIG. 3, FIG. 20, FIG. 21 and FIG. 22, the biometric determination operation is described below.

First, at step S400, the control unit 3, at the interval q, causes the light irradiation device 111 to be turned off and the image processing unit 3a acquires, from the image acquisition device 104, a plurality of pieces of image information I3 with respect to the measuring object 1a. Then, the image processing unit 3a, based on the total image information of the plurality of pieces of image information I3, acquires the spectroscopic information and calculates spectroscopic image information B.

Next, at step S401, the control unit 3, at the interval p, causes the light irradiation device 111 to be lighted and the image processing unit 3a acquires, from the image acquisition device 104, a plurality of pieces of image information I4 with respect to the measuring object 1a. Then, the image processing unit 3a, based on the total image information of the plurality of pieces of image information I4, acquires the spectroscopic information and calculates spectroscopic image information C.

Figure 23:
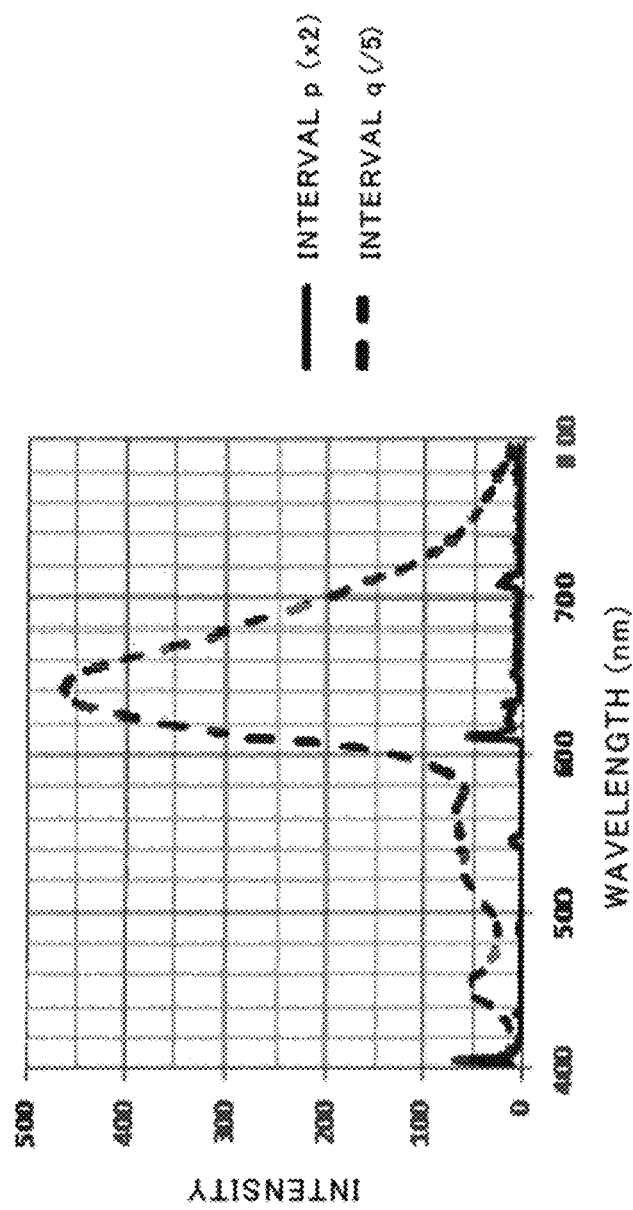
FIG. 23 is a drawing illustrating one example of a spectrum of spectroscopic image information calculated by the living body determination device illustrated in FIG. 20.

FIG. 23 illustrates one example of the spectrums that are calculation results of the spectroscopic image information B and the spectroscopic image information C. In FIG. 23, a horizontal axis represents the wavelength and a vertical axis represents an intensity of a reflected light. A measurement example of the spectroscopic information when the measuring object 1a is the "living body" (here cheek r2) is illustrated. Here, the spectroscopic information represents the spectrum of the reflected light intensity. The spectroscopic image information B at the interval q is represented with the solid line. Note that the value represented with the solid line is obtained by dividing an actual value by 5. The spectroscopic image information C at the interval p is represented with the broken line. Note that the value represented by the broken line is obtained by multiplying the actual value by 2.

At step S402, the image processing unit 3a, from the spectroscopic image information B and the spectroscopic image information C, calculates the spectroscopic image information A. Specifically, by subtracting, from the spectroscopic image information C, the spectroscopic image information B, the spectroscopic image information A is calculated.

Next, at step S403, the biometric authenticity determination unit 3b determines whether the spectrum of the spectroscopic image information A satisfies the predetermined condition. Specifically, the biometric authenticity determination unit 3b determines whether the absorbency of the spectroscopic image information A is the predetermined value or above, whether the degree of correlation calculated from the spectrum of the spectroscopic image information A and the biological determination spectrum is the predetermined value or above, and whether a ratio of a plurality of components with respect to the living body of the biological determination spectrum is the predetermined value or above.

When at step S403, it is determined that the predetermined condition is satisfied, at step S404, the biometric authenticity determination unit 3b determines that the measuring object 1a is the living body and outputs a fact that the biometric authenticity determination is "true" to the output unit 6.

Alternatively, at step S403, when it is determined that the predetermined condition is not satisfied, at step S405, the biometric authenticity determination unit 3b determines that the measuring object 1a is not the living body and outputs a fact that the biometric authenticity determination is "false" to the output unit 6.

According to the living body determination device of the present example embodiment, in addition to the effects described in the first example embodiment, it is possible to remove influences of the external light and improve the accuracy.

To the living body determination device according to the present example embodiment also, the variation described in the first example embodiment can be applied. For example, it is possible to replace operations of the interval p and the interval q illustrated in FIG. 21 and replace step S400 and step S401 for the operation.

Fourth application example: biometric authentication device

Next, a biometric authentication device to which the above described living body determination device according to the fourth example embodiment is applied is described.

The computing device 105 of the biometric authentication device of this example also has the configuration illustrated in FIG. 10.

Figure 24:
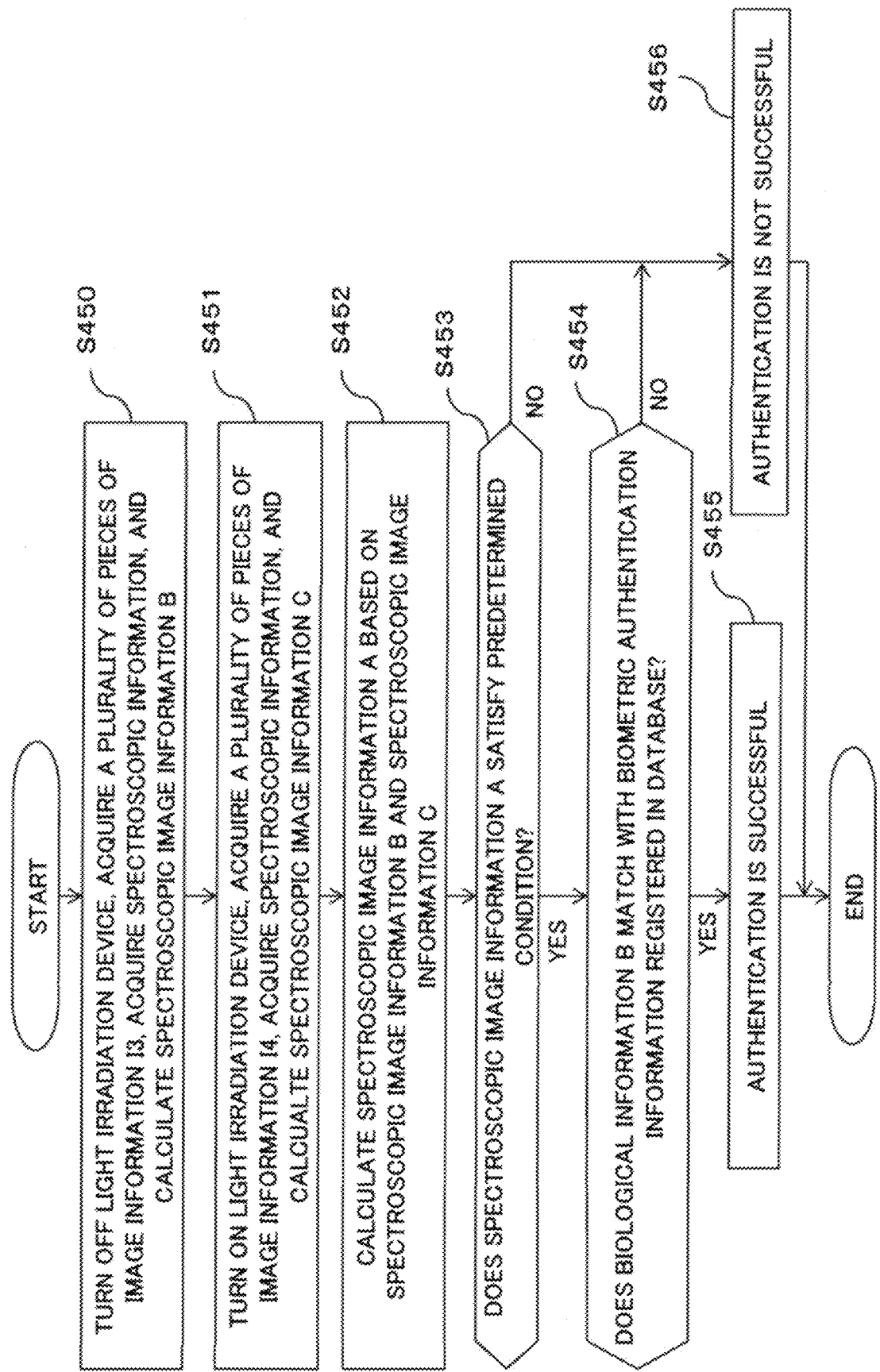
FIG. 24 is a flowchart illustrating one procedure of a biometric authentication operation of a biometric authentication device that is a fourth application example in which the living body determination device according to the fourth example embodiment of the disclosed subject matter is applied.

FIG. 24 illustrates one procedure of the biometric authentication operation.

First, at step S450, the control unit 13, at the interval q, causes the light irradiation device 111 to be turned off, and the image processing unit 13a acquires, from the image acquisition device 104, the plurality of pieces of image information I3 with respect to the measuring object 1a. The image processing unit 13a, based on the total image information of the plurality of pieces of image information I3, acquires the spectroscopic information and calculates the spectroscopic image information B.

Next, at step S451, the control unit 13, at the interval p, causes the light irradiation device 111 to be lighted and the image processing unit 13a, from the image acquisition device 104, acquires the plurality of pieces of image information I4 with respect to the measuring object 1a. Then, the image processing unit 13a, based on the total image information of the plurality of pieces of image information I4, acquires the spectroscopic information and calculates the spectroscopic image information C.

At step S452, the image processing unit 13a, from the spectroscopic image information B and the spectroscopic image information C, calculates the spectroscopic image information A. Specifically, the image processing unit 13a, by subtracting, from the spectroscopic image information C, the spectroscopic image information B, calculates the spectroscopic image information A.

Next, at step S453, the biometric authenticity determination unit 13b determines whether the spectrum of the spectroscopic image information A satisfies the predetermined condition. Specifically, the biometric authenticity determination unit 13b determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

When the answer to the determination at step S453 is "Yes," at step S454, the biometric authentication unit 13c acquires, from the memory 14, the biometric authentication information and determines whether the feature information matches with the biometric authentication information. When the feature information matches with the biometric authentication information, at step S455, the biometric authentication unit 13c determines that a person is an authorized person and outputs information representing that the authentication is successful to the output unit 16.

When the answer to the determination at step S453 or step S454 is "No," at step S456, the biometric authentication unit 13c determines that a person is not an authorized person and outputs information representing the authentication error to the output unit 16.

Note that, in the above described biometric authentication operation, the order of step S450 and step S451 may be changed.

According to the living body determination device of the present example embodiment, in addition to effects described in the first example embodiment, it is possible to remove influences of the external light and improve the accuracy.

Also to the biometric authentication device of this example, a configuration and a variation described in the first application example can be applied.

Fifth Example Embodiment

Figure 25:
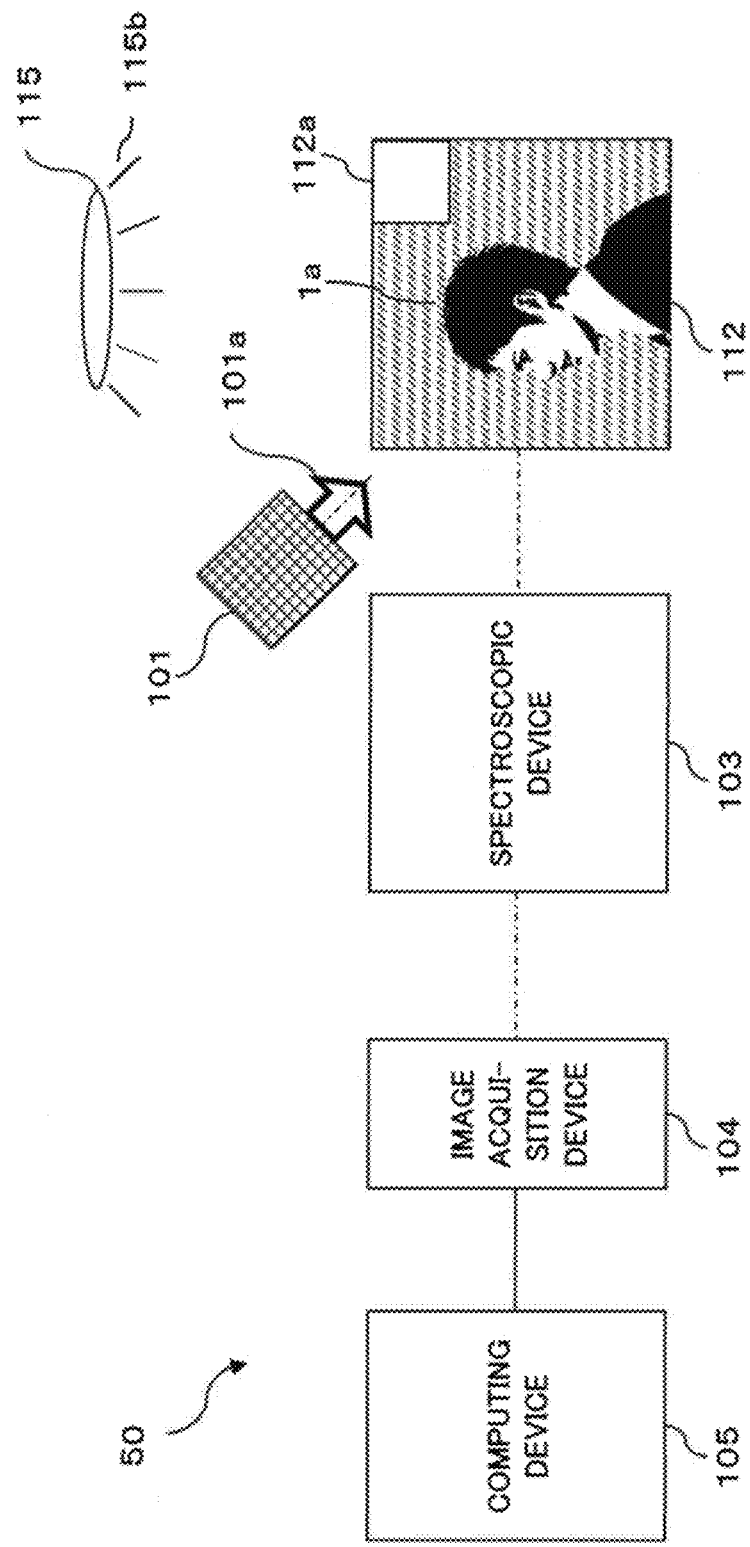
FIG. 25 is a block diagram illustrating a configuration of a living body determination device according to a fifth example embodiment of the disclosed subject matter.

FIG. 25 is a block diagram illustrating a configuration of the living body determination device according to the fifth example embodiment of the disclosed subject matter.

Referring to FIG. 25, a living body determination device 50 includes a light irradiation device 101, a target installation device 112, a spectroscopic device 103, an image acquisition device 104, and a computing device 105. The light irradiation device 101, the spectroscopic device 103, the image acquisition device 104, and the computing device 105 are the same as the devices described in the first example embodiment. A configuration different from that of the first example embodiment is mainly described below, and descriptions of the same configuration are omitted.

The target installation device 112 is a target installation unit that places the position of the measuring object 1a within the predetermined range. For example, the seat for sitting the measuring object 1a and the display unit for instructing a position to stand to the measuring object 1a are included. Here, the measuring object 1a is a part of the body (for example, upper body, cephalic region, face and the like). In FIG. 25, as one example of the measuring object 1a, the cephalic region is schematically illustrated.

The target installation device 112 further includes a reference unit 112a. The reference unit 112a reflects light without changing the spectrum of the light 101a of the light irradiation device 101. For example, as the reference unit 112a, a standard white plate can be used. The reference unit 112a is provided to a part of the target installation device 112 and also provided to a position in which the image acquisition device 104 can acquire image information with respect to the reference unit 112a when the measuring object is present at the target installation device 112.

Next, the biometric determination operation of the living body determination device according to the present example embodiment is specifically described.

Figure 26:
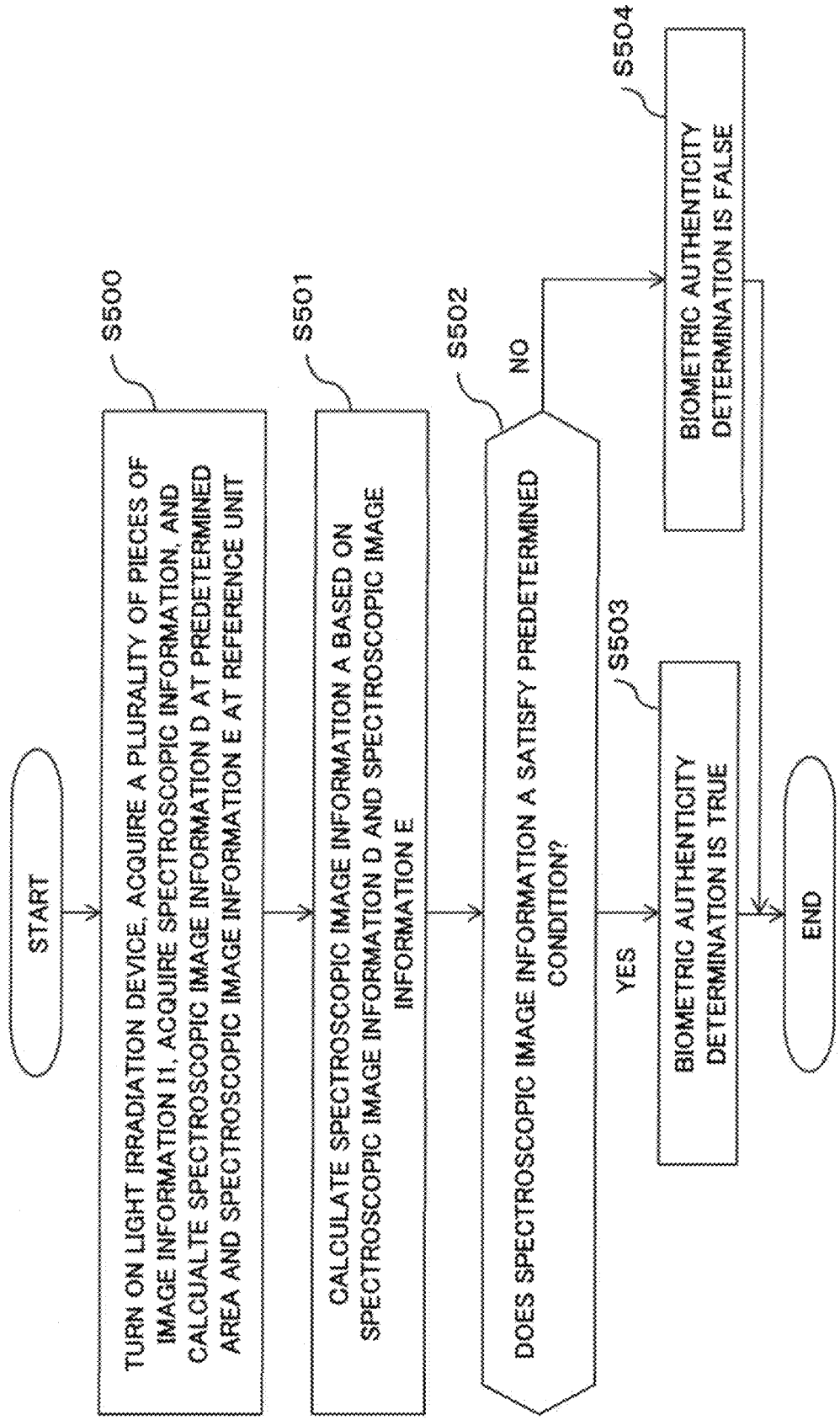
FIG. 26 is a flowchart illustrating one procedure of a biometric determination operation of the living body determination device illustrated in FIG. 25.

FIG. 26 illustrates one procedure of the biometric determination operation. With reference to FIG. 3, FIG. 25 and FIG. 26, the biometric determination operation is described below.

First, at step S500, the control unit 3 causes the light irradiation device 101 to be lighted and the image processing unit 3a acquires, from the image acquisition device 104, the plurality of pieces of image information I1 with respect to the measuring object 1a. The image processing unit 3a, based on the total image information of the plurality of pieces of image information I1, acquires the spectroscopic information and calculates spectroscopic image information D at the predetermined areas and spectroscopic image information E at the reference unit 112a. The predetermined areas are, for example, r1(forehead), r2(cheek), r3(ear), r4(nose), r5(lip), r6(jaw), and r7(neck) illustrated in FIG. 4A.

Figure 27:
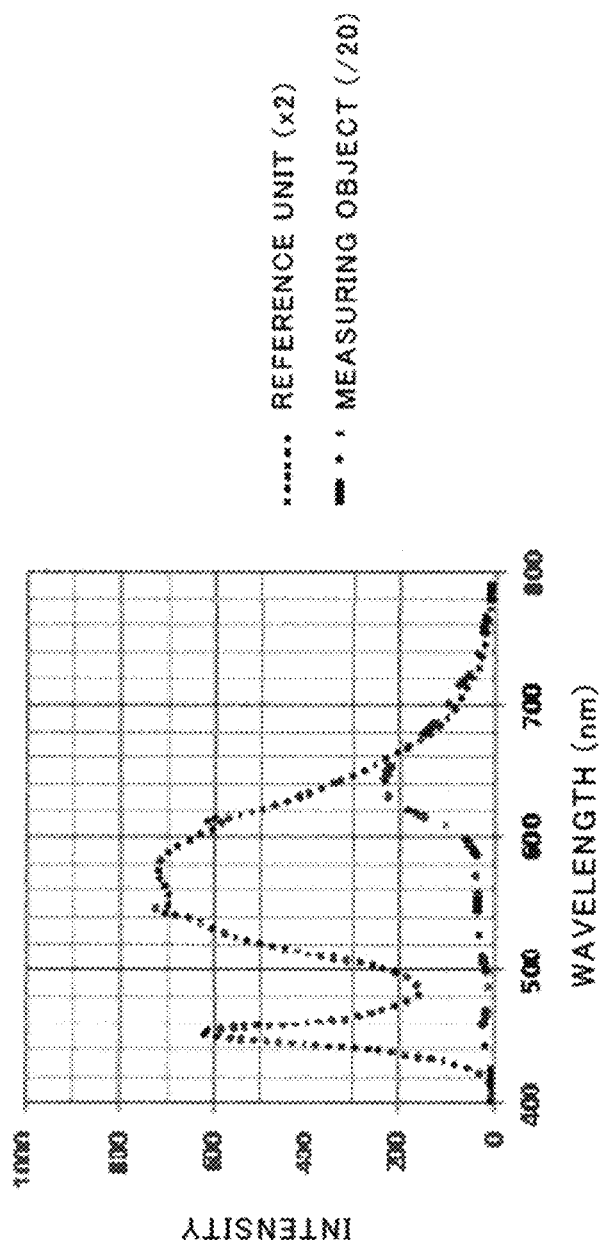
FIG. 27 is a drawing illustrating one example of a spectrum of spectroscopic image information calculated by the living body determination device illustrated in FIG. 25.

FIG. 27 illustrates one example of the spectrum that is the calculation result of the spectroscopic image information D and the spectroscopic image information E. In FIG. 27, the horizontal axis represents the wavelength and the vertical axis represents the reflected light intensity. The measurement example of the spectroscopic information when the measuring object 1a is the "living body" (here cheek r2) is illustrated. Here, the spectroscopic information represents the spectrum of the reflected light intensity. The spectroscopic image information D at the predetermined areas is represented with the solid line. Note that a value represented by the solid line is obtained by multiplying an actual value by 2. The spectroscopic image information E at the reference unit 112a is represented with the dot-line. Note that a value represented by the dot-line is obtained by dividing an actual value by 20.

Next, at step S01, the image processing unit 3a, from the spectroscopic image information D and the spectroscopic image information E, calculates the spectroscopic image information A. Specifically, by dividing the spectroscopic image information E by the spectroscopic image information D, the spectroscopic image information A is calculated.

At step S502, the biometric authenticity determination unit 3b determines whether the spectrum of the spectroscopic image information A satisfies the predetermined condition. Specifically, the biometric authenticity determination unit 3b determines whether the absorbency of the spectroscopic image information A is the predetermined value or above, whether the degree of correlation calculated from the spectrum of the spectroscopic image information A and the biological determination spectrum is the predetermined value or above, and whether a ratio of a plurality of components with respect to the living body of the biological determination spectrum is the predetermined value or above.

When at step S502, it is determined that the predetermined condition is satisfied, at step S503, the biometric authenticity determination unit 3b determines that the measuring object 1a is the living body and outputs a fact that the biometric authenticity determination is "true" to the output unit 6.

When at step S502, it is determined that the predetermined condition is not satisfied, at step S504, the biometric authenticity determination unit 3b determines that the measuring object 1a is not the living body and outputs a fact that the biometric authenticity determination is "false" to the output unit 6.

According to the living body determination device of the present example embodiment, in addition to effects described in the first example embodiment, it is possible to remove influences of the external light and improve the accuracy.

To the living body determination device according to the present example embodiment also, the variation described in the first example embodiment can be applied.

Fifth application example: biometric authentication device

Next, a biometric authentication device to which the above described living body determination device according to the fifth example embodiment is applied is described.

The computing device 105 of the biometric authentication device of this example also has the configuration illustrated in FIG. 10.

Figure 28:
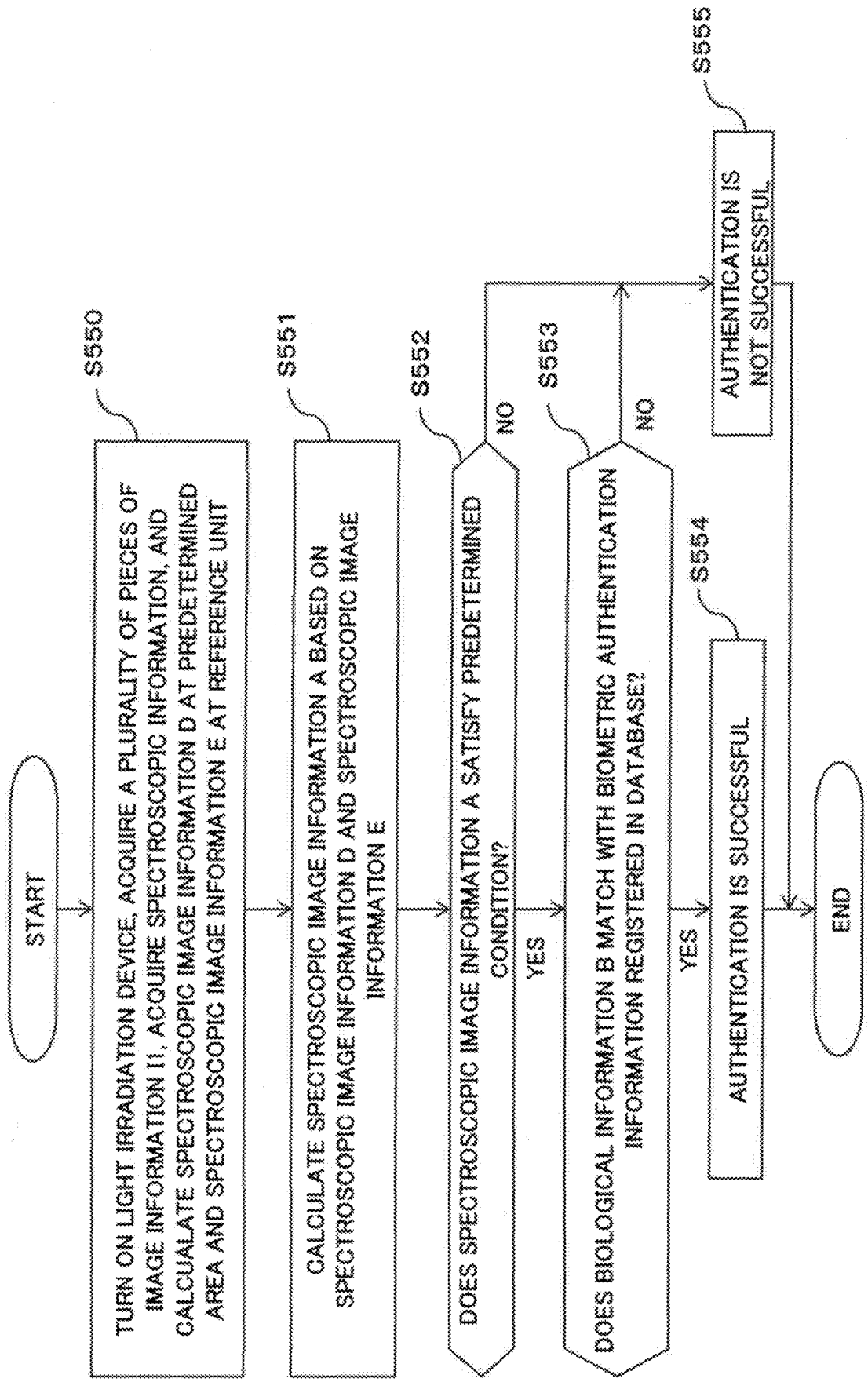
FIG. 28 is a flowchart illustrating one procedure of a biometric authentication operation of a biometric authentication device that is a fifth application example in which the living body determination device according to the fifth example embodiment of the disclosed subject matter is applied.

FIG. 28 illustrates one procedure of the biometric authentication operation.

First, at step S550, the control unit 13 causes the light irradiation device 101 to be lighted and the image processing unit 13*a* acquires, from the image acquisition device 104, the plurality of pieces of image information I1 with respect to the measuring object 1*a*. Then, the image processing unit 13*a*, based on the total image information of the plurality of pieces of image information I1, acquires the spectroscopic information and calculates the spectroscopic image information D at the predetermined areas and the spectroscopic image information E at the reference unit.

Next, at step S551, the image processing unit 13*a*, from the spectroscopic image information D and the spectroscopic image information E, calculates the spectroscopic image information A. Specifically, the image processing unit 13*a*, by dividing the spectroscopic image information E by the spectroscopic image information D, calculates the spectroscopic image information A.

Next, at step S552, the biometric authenticity determination unit 13*b* determines whether the spectrum of the spectroscopic image information A satisfies the predetermined condition. Specifically, the biometric authenticity determination unit 13*b* determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

When the answer to the determination at step S552 is "Yes," at step S553, the biometric authentication unit 13*c* acquires, from the memory 14, the biometric authentication information and determines whether the feature information matches with the biometric authentication information. When the feature information matches with the biometric authentication information, at step S554, the biometric authentication unit 13*c* determines that a person is an authorized person and outputs information representing that the authentication is successful to the output unit 16.

When the answer to the determination at step S552 or step S553 is "No," at step S555, the biometric authentication unit 13*c* determines that a person is not an authorized person and outputs information representing the authentication error to the output unit 16.

According to the living body determination device of the present example embodiment, in addition to the effects described in the first example embodiment, it is possible to remove the influences of the external light and improve the accuracy.

To the biometric authentication device of this example also, a configuration and a variation described in the first application example can be applied.

Sixth Example Embodiment

Figure 29:
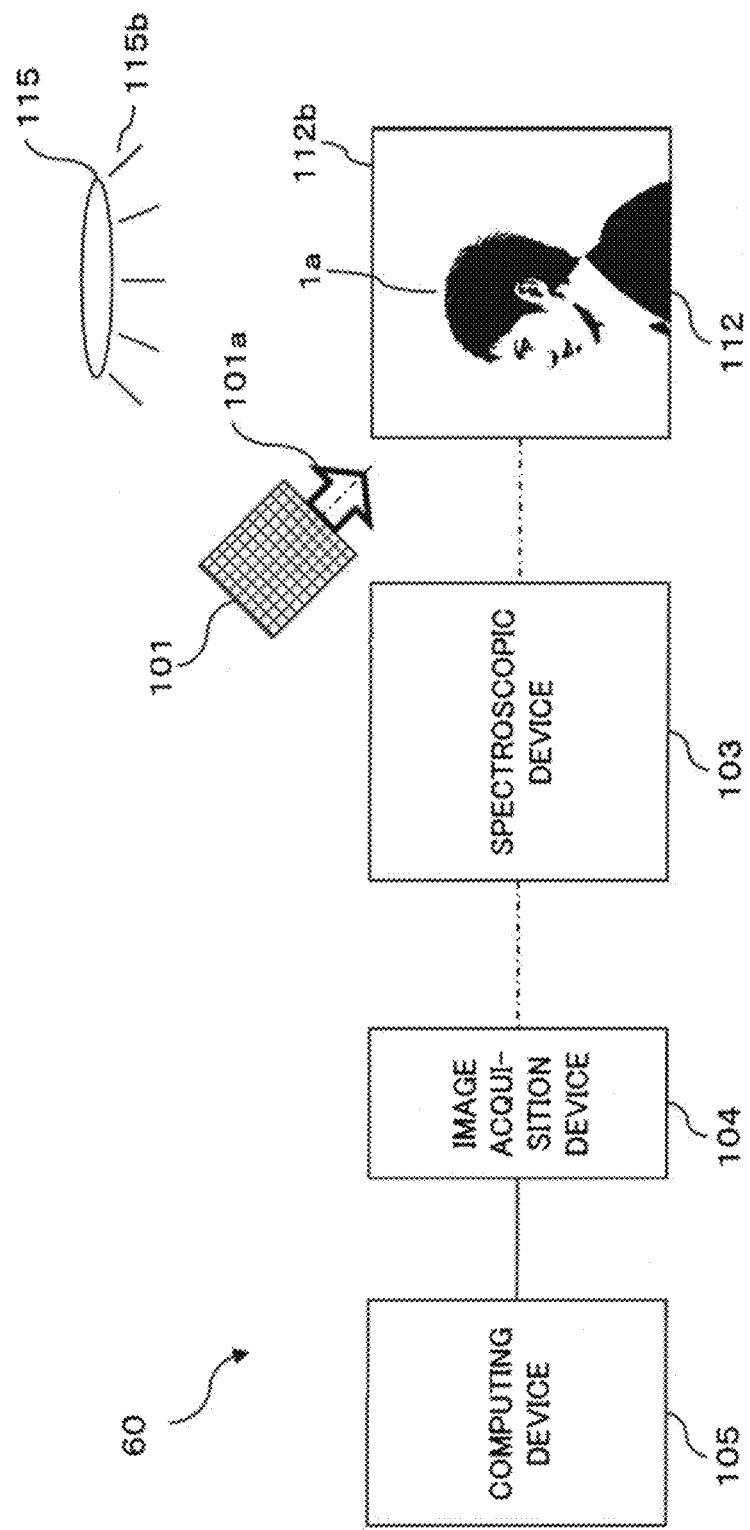
FIG. 29 is a block diagram illustrating a configuration of a living body determination device according to a sixth example embodiment of the disclosed subject matter.

FIG. 29 is a block diagram illustrating a configuration of the living body determination device according to the sixth example embodiment of the disclosed subject matter.

Referring to FIG. 29, a living body determination device 60 includes a light irradiation device 101, a target installation device 112, a spectroscopic device 103, an image acquisition device 104, and a computing device 105. The light irradiation device 101, the spectroscopic device 103, the image acquisition device 104 and the computing device 105 are the same as the devices described in the first example embodiment. A configuration different from that of the first example embodiment is mainly described below, and descriptions of the same configuration are omitted.

The target installation device 112 is a target installation unit for placing a position of the measuring object 1*a* within the predetermined range. For example, the seat for sitting the measuring object and the display for instructing a position to stand to the measuring object are included. Here, the measuring object 1*a* is a part of the body (for example, upper body, cephalic region, face and the like). FIG. 29 schematically illustrates the cephalic region as one example of the measuring object 1*a*.

The target installation device 112 further includes a reference unit 112*b*. The reference unit 112*b* reflects the light without changing the spectrum of the light 101*a* of the light irradiation device 101. For example, as the reference unit 112*b*, a standard white plate can be used. The reference unit 112*b* is arranged on a substantially entire surface of the target installation device 112.

Next, the biometric determination operation of the living body determination device according to the present example embodiment is specifically described.

Figure 30:
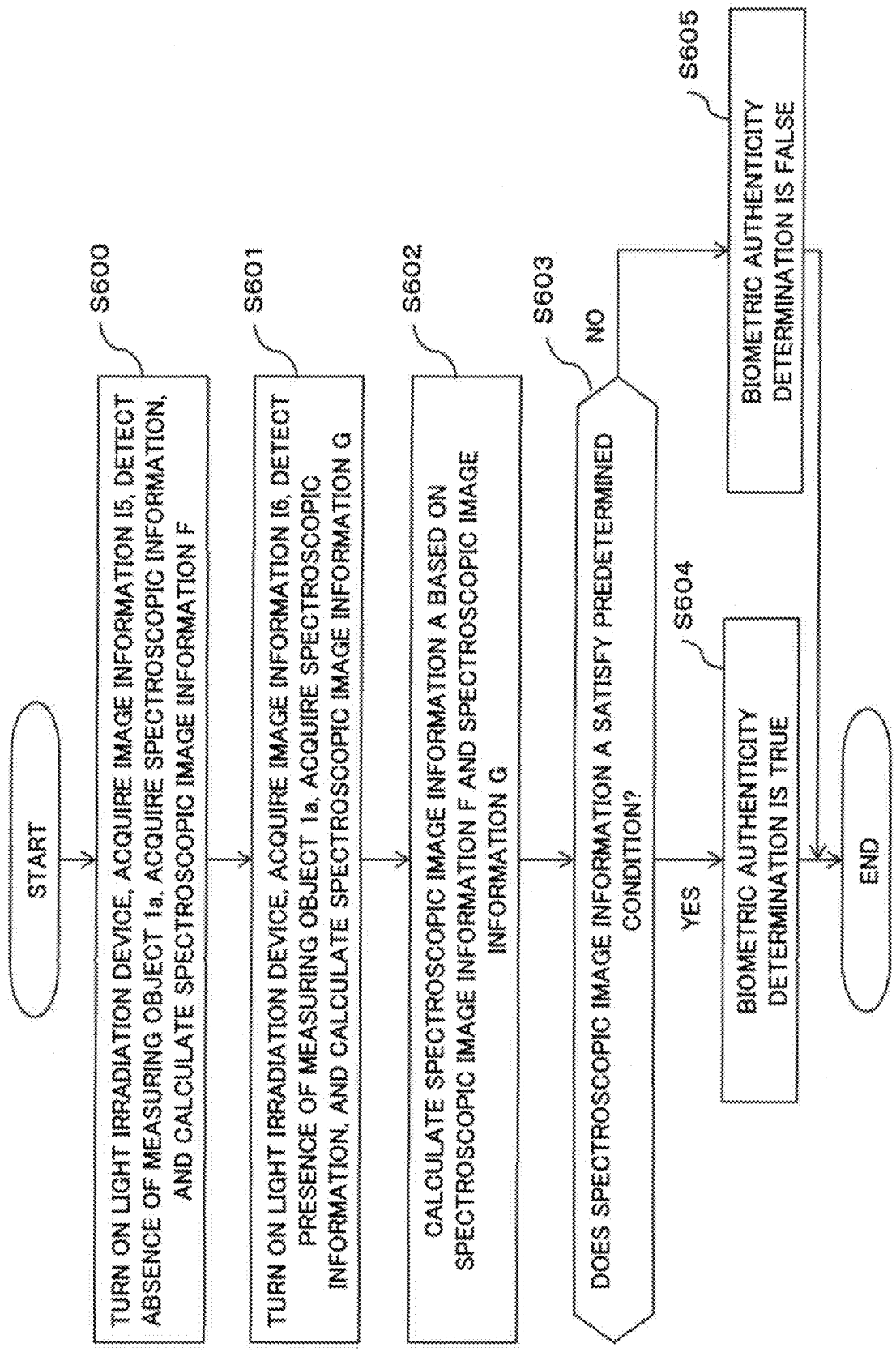
FIG. 30 is a flowchart illustrating one procedure of a biometric determination operation of the living body determination device illustrated in FIG. 28.

FIG. 30 illustrates one procedure of the biometric determination operation. With reference to FIG. 3, FIG. 29 and FIG. 30, the biometric determination operation is described below.

First, at step S600, the image processing unit 3*a*, during a period in which the measuring object 1*a* is absent, acquires spectroscopic image information F. Specifically, first, the control unit 3 causes the light irradiation device 101 to be lighted, and the image processing unit 3*a*, based on the image information from the image acquisition device 104, detects the absence of the measuring object 1*a*. Here, the absence of the measuring object 1*a* can be detected by, for example, periodically acquiring image information and confirming whether a plurality of pixels of image information extracted at a certain time have the substantially same spectrum. Other absence detection methods include a method of detecting, with an infrared radiation sensor or the like, that the measuring object 1*a* passes the specific area of the target installation device 112 and a method of detecting the absence by the operation of the measuring object 1*a*.

When the absence of the measuring object 1*a* is detected, the image processing unit 3*a* acquires, from the image acquisition device 104, a plurality of pieces of image information I5. Then, the image processing unit 3*a*, based on the total image information of the plurality of pieces of image information I5, acquires the spectroscopic information and calculates the spectroscopic image information F at the predetermined areas.

Next, at step S601, the image processing unit 3*a*, during a period in which the measuring object 1*a* is present, acquires spectroscopic image information G. Specifically, first the control unit 3 causes the light irradiation device 101 to be lighted and the image processing unit 3*a*, based on the image information from the image acquisition device 104, detects the presence of the measuring object 1*a*. To this detection also, a method similar to that for the absence detection described in step S600 can be applied.

When the presence of the measuring object 1a is detected, the control unit 3 causes the light irradiation device 101 to be lighted and the image processing unit 3a acquires, from the image acquisition device 104, a plurality of pieces of image information I6. Then, the image processing unit 3a, based on the total image information of the plurality of pieces of image information I6, acquires the spectroscopic information and calculates the spectroscopic image information G at the predetermined areas.

Figure 31:
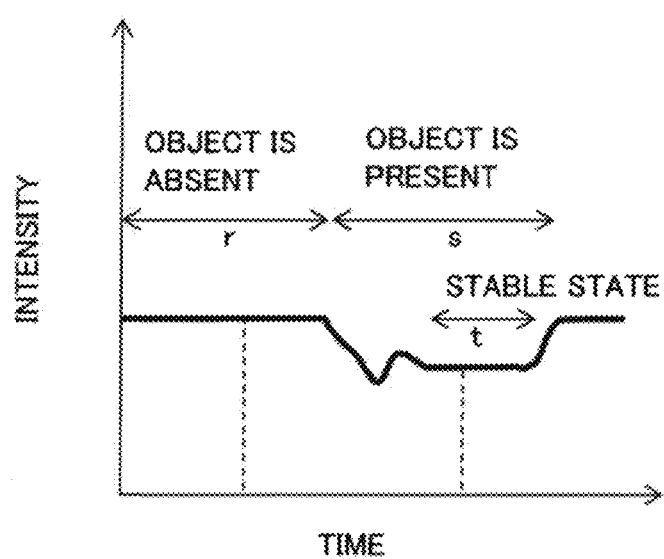
FIG. 31 is a drawing illustrating time changes of the intensity at a certain pixel and a certain wavelength of the spectroscopic image information acquired by the living body determination device illustrated in FIG. 28.

Note that immediately after a state in which the measuring object 1a is absent changes to a state in which the measuring object 1a is present, the light intensity of the pixel largely fluctuates, and thereafter with a lapse of time, the fluctuation quantity of the light intensity gradually becomes small. FIG. 31 illustrates changes of the light intensity of the certain wavelength of the certain pixel of the spectroscopic image information when the absent state is changed to the present state. The interval r represents a period in which the measuring object 1a is absent and the interval s represents a period in which the measuring object 1a is present. The interval t represents a period in which the light intensity of the pixel in the interval s is stable. In the presence detection of step S600, the image processing unit 3a detects the interval s (desirably interval t).

Next, at step S602, the image processing unit 3a, based on the spectroscopic image information F and the spectroscopic image information G, calculates the spectroscopic image information A. Specifically, the image processing unit 3a, by dividing the spectroscopic image information F by the spectroscopic image information G, calculates the spectroscopic image information A.

Next, at step S603, the biometric authenticity determination unit 3b determines whether the spectrum of the spectroscopic image information A satisfies the predetermined condition. Specifically, the biometric authenticity determination unit 3b determines whether the absorbency of the spectroscopic image information A is the predetermined value or above, whether the degree of correlation calculated from the spectrum of the spectroscopic image information A and the biological determination spectrum is the predetermined value or above, and whether a ratio of a plurality of components with respect to the living body of the biological determination spectrum is the predetermined value or above.

When at step S603, it is determined that the predetermined condition is satisfied, at step S604, the biometric authenticity determination unit 3b determines that the measuring object 1a is the living body and outputs a fact that the biometric authenticity determination is "true" to the output unit 6.

Alternatively, when at step S603, it is determined that the predetermined condition is not satisfied, at step S605, the biometric authenticity determination unit 3b determines that the measuring object 1a is not the living body and outputs a fact that the biometric authenticity determination is "false" to the output unit 6.

According to the living body determination device of the present example embodiment, in addition to the effects described in the first example embodiment, it is possible to remove the influences of the external light and improve the accuracy.

To the living body determination device according to the present example embodiment also, the variation described in the first example embodiment can be applied.

Sixth application example: biometric authentication device

Next, a biometric authentication device to which the above described living body determination device according to the sixth example embodiment is applied is described.

The computing device 105 of the biometric authentication device of this example also has the configuration illustrated in FIG. 10.

Figure 32:
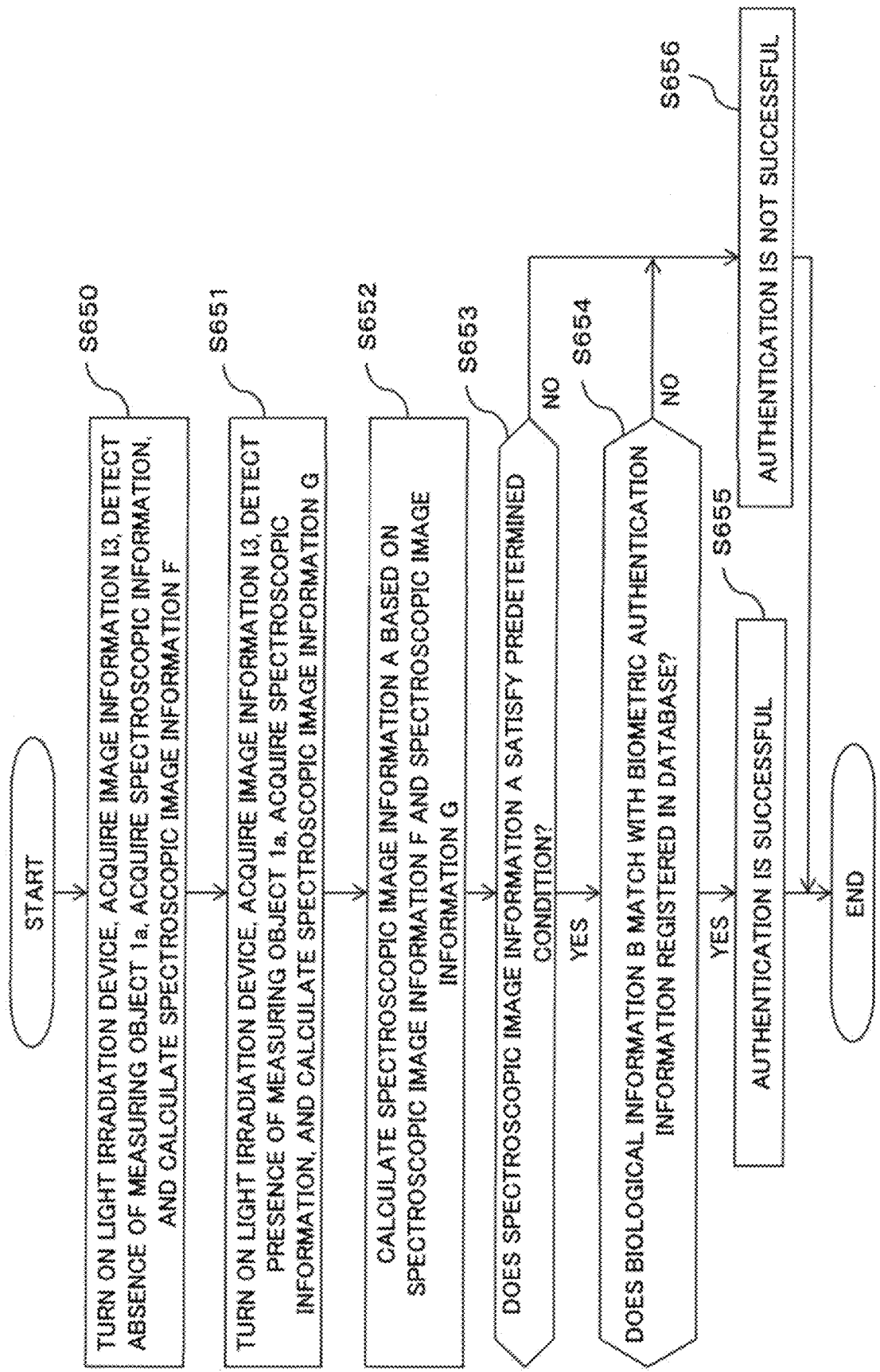
FIG. 32 is a flowchart illustrating one procedure of a biometric authentication operation of a biometric authentication device that is a sixth application example in which the living body determination device according to the sixth example embodiment of the disclosed subject matter is applied.

FIG. 32 illustrates one procedure of the biometric authentication operation.

First, at step S650, the image processing unit 13a, during a period in which the measuring object 1a is absent, acquires the spectroscopic image information F. Specifically, first the image processing unit 13a, based on the image information from the image acquisition device 104, detects the absence of the measuring object 1a, i.e., the interval r illustrated in FIG. 31. For this detection method also, the method described in the fifth application example is used.

When the absence of the measuring object 1a is detected, the control unit 13 causes the light irradiation device 101 to be lighted and the image processing unit 13a acquires, from the image acquisition device 104, the plurality of pieces of image information I5. Then, the image processing unit 13a, based on the total image information of the plurality of pieces of image information I5, acquires the spectroscopic information and calculates the spectroscopic image information F at the predetermined areas.

Next, at step S651, the image processing unit 13a, during a period in which the measuring object 1a is present, acquires the spectroscopic image information G. Specifically, first the control unit 13 causes the light irradiation device 101 to be lighted and the image processing unit 13a, based on the image information from the image acquisition device 104, detects the presence of the measuring object 1a, i.e., the interval s illustrated in FIG. 31 (desirably interval t). To this detection also, a method similar to that for the presence detection described in step S601 can be applied.

When the presence of the measuring object 1a is detected, the control unit 13 causes the light irradiation device 101 to be lighted and the image processing unit 13a acquires, from the image acquisition device 104, the plurality of pieces of image information I6. Then, the image processing unit 13a, based on the total image information of the plurality of pieces of image information I6, acquires the spectroscopic information and calculates the spectroscopic image information G at the predetermined areas.

Next, at step S652, the image processing unit 13a, based on the spectroscopic image information F and the spectroscopic image information G, calculates the spectroscopic image information A. Specifically, the image processing unit 13a, by dividing the spectroscopic image information F by the spectroscopic image information G, calculates the spectroscopic image information A.

Next, at step S653, the biometric authenticity determination unit 13b determines whether the spectrum of the spectroscopic image information A satisfies the predetermined condition. Specifically, the biometric authenticity determination unit 13b determines whether the absorbency of the spectroscopic image information A is higher than the predetermined value, whether the degree of correlation calculated from the spectrum of the spectroscopic image information A and the biological determination spectrum is the predetermined value or above, and whether a ratio of a plurality of components with respect to the living body of the biological determination spectrum is higher than the predetermined value.

When the answer to the determination at step S653 is "Yes," at step S654, the biometric authentication unit 13c acquires, from the memory 14, the biometric authentication information and determines whether the feature information matches with the biometric authentication information. When the feature information matches with the biometric authentication information, at step S655, the biometric authentication unit 13c determines that a person is an authorized person and outputs information representing that the authentication is successful to the output unit 16.

When the answer to the determination at step S653 or step S654 is "No," at step S656, the biometric authentication unit 13c determines that a person is not an authorized person and outputs information representing the authentication error to the output unit 16.

According to the living body determination device of the present example embodiment, in addition to the effects described in the first example embodiment, it is possible to remove the influences of the external light and improve the accuracy.

To the biometric authentication device of this example also, a configuration and a variation described in the first application example can be applied.

The example embodiments and the application examples of the disclosed subject matter have been described above as exemplary examples. However, the disclosed subject matter is not limited to the above described example embodiments and application examples, and to the configurations and the operations, various aspects that can be understood by a person skilled in the art can be applied.

Further, although the disclosed subject matter takes forms such as supplementary notes 1 to 26 below, the disclosed subject matter is not limited to these forms.

[Supplementary note 1]

A living body determination device includes:

light irradiation means for irradiating a measuring object with a first light including a plurality of spectrums;

spectroscopic means for dispersing a light at intensity depending on a wavelength and outputting the light;

image acquisition means for receiving the light output by the spectroscopic means and outputting image information representing brightness depending on the intensity of the light; and a control unit that, for each spectrum of the first light, acquires image information with respect to the measuring object from the image acquisition means, based on the image information, selects one or more areas, for each of the areas, acquires spectroscopic information, and based on whether the spectroscopic information satisfies a predetermined condition, determines whether the measuring object is a living body.

[Supplementary note 2]

The living body determination device according to supplementary note 1, wherein the control unit, based on a comparison result between the spectroscopic information and a predetermined spectral characteristic, determines whether the measuring object is a living body.

[Supplementary note 3]

The living body determination device according to supplementary note 2, wherein the predetermined spectral characteristic is a combination of a spectrum of a plurality of components with respect to a living body.

[Supplementary note 4]

The living body determination device according to supplementary note 3, wherein the control unit, based on a ratio of a plurality of components with respect to the living body, determines whether the measuring object is a living body.

[Supplementary note 5]

The living body determination device according to any one of supplementary notes 1 to 4, wherein the control unit, based on an absolute value of the spectroscopic information, determines whether the measuring object is a living body.

[Supplementary note 6]

The living body determination device according to any one of supplementary notes 1 to 5, wherein the light irradiation means includes an irradiation position control unit that, based on the areas, controls an irradiation position of the first light.

[Supplementary note 7]

The living body determination device according to any one of supplementary notes 1 to 6, further includes:

a target installation unit that places a position of the measuring object within a predetermined range.

[Supplementary note 8]

The living body determination device according to supplementary note 7, wherein the control unit, based on the areas, controls the predetermined range.

[Supplementary note 9]

The living body determination device according to any one of supplementary notes 1 to 8, wherein the control unit, in a state where the light irradiation means is turned off, acquires first spectroscopic image information including spectroscopic information for each of the areas, in a state where the light irradiation device is lighted, acquires second spectroscopic image information including spectroscopic information for each of the areas, and based on the first and second spectroscopic image information, determines whether the measuring object is a living body.

[Supplementary note 10]

The living body determination device according to supplementary note 7 or 8, wherein the target installation unit includes a reference unit that reflects an incident light without changing a spectrum; and the control unit, for each spectrum of the first light, acquires image information on the reference unit from the image acquisition means, based on the image information, acquires spectroscopic information of the reference unit, and based on spectroscopic information for each of the areas and spectroscopic information of the reference unit, determines whether the measuring object is a living body.

[Supplementary note 11]

The living body determination device according to any one of supplementary notes 7, 8 and 10 wherein the control unit, in a state where the measuring object is not present in the target installation unit, acquires first spectroscopic image information including spectroscopic information for each of the areas, in a state where the measuring object is present in the target installation unit, acquires second spectroscopic image information including spectroscopic information for each of the areas, and based on the first and second spectroscopic image information, determines whether the measuring object is a living body.

[Supplementary note 12]

A living body determination method conducted in a device includes light irradiation means for irradiating a measuring object with a first light including a plurality of spectrums, spectroscopic means for dispersing a light at intensity depending on a wavelength and outputting the light, and image acquisition means for receiving the light output by the spectroscopic means and outputting image information representing brightness depending on the intensity of the light, the living body determination method includes:

for each spectrum of the first light, acquiring image information on the measuring object from the image acquisition means;

based on the image information, selecting one or more areas and for each of the areas, acquiring spectroscopic information; and based on whether the spectroscopic information satisfies a predetermined condition, determining whether the measuring object is a living body.

[Supplementary note 13]

A living body determination program for causing a computer of a device includes light irradiation means for irradiating a measuring object with a first light including a plurality of spectrums, spectroscopic means for dispersing a light at intensity depending on a wavelength and outputting the light, and image acquisition means for receiving the light output by the spectroscopic means and outputting image information representing brightness depending on the intensity of the light, to execute the processes of:

for each spectrum of the first light, acquiring image information on the measuring object from the image acquisition means;

based on the image information, selecting one or more areas and for each of the areas, acquiring spectroscopic information; and based on whether the spectroscopic information satisfies a predetermined condition, determining whether the measuring object is a living body.

[Supplementary note 14]

A biometric authentication device includes:

light irradiation means for irradiating a measuring object with a first light including a plurality of spectrums;

spectroscopic means for dispersing a light at intensity depending on a wavelength and outputting the light;

image acquisition means for receiving the light output by the spectroscopic means and outputting image information representing brightness depending on the intensity of the light; and a control unit that, for each spectrum of the first light, acquires image information on the measuring object from the image acquisition means, based on the image information, selects one or more areas, for each of the areas, acquires spectroscopic information, and based on whether the spectroscopic information satisfies a predetermined condition, determines whether the measuring object is a living body, wherein the control unit, when the measuring object is determined to be a living body, acquires, from the image information, biological information representing a physical feature, determines whether the biological information matches with authentication biometric information registered in advance, when the biological information matches with the authentication biometric information registered in advance, determines that an authentication is successful, and when the biological information does not match with the authentication biometric information registered in advance, determines that the authentication is not successful.

[Supplementary note 15]

The biometric authentication device according to supplementary note 14, wherein the control unit, based on a comparison result between the spectroscopic information and a predetermined spectral characteristic, determines whether the measuring object is a living body.

[Supplementary note 16]

The biometric authentication device according to supplementary note 15, wherein the predetermined spectral characteristic is a combination of a spectrum of a plurality of components with respect to a living body.

[Supplementary note 17]

The living body determination device according to supplementary note 16, wherein the control unit, based on a ratio of a plurality of components with respect to the living body, determines whether the measuring object is the living body.

[Supplementary note 18]

The biometric authentication device according to any one of supplementary notes 14 to 17, wherein the control unit, based on an absolute value of the spectroscopic information, determines whether the measuring object is a living body.

[Supplementary note 19]

The biometric authentication device according to any one of supplementary notes 14 to 18, wherein the light irradiation means includes an irradiation position control unit that, based on the areas, controls an irradiation position of the first light.

[Supplementary note 20]

The biometric authentication device according to any one of supplementary notes 14 to 19, further includes:

a target installation unit that places a position of the measuring object within a predetermined range.

[Supplementary note 21]

The biometric authentication device according to supplementary note 20, wherein the control unit, based on the areas, controls the predetermined range.

[Supplementary note 22]

The biometric authentication device according to any one of supplementary notes 14 to 21, wherein the control unit, in a state where the light irradiation means is turned off, acquires first spectroscopic image information including spectroscopic information for each of the areas, in a state where the light irradiation device is lighted, acquires second spectroscopic image information including spectroscopic information for each of the areas, and based on the first and second spectroscopic image information, determines whether the measuring object is a living body.

[Supplementary note 23]

The biometric authentication device according to supplementary note 20 or 21, wherein the target installation unit includes a reference unit that reflects an incident light without changing a spectrum; and the control unit, for each spectrum of the first light, acquires image information with respect to the reference unit from the image acquisition means, based on the image information, acquires spectroscopic information of the reference unit, and based on spectroscopic information for each of the areas and spectroscopic information of the reference unit, determines whether the measuring object is a living body.

[Supplementary note 24]

The biometric authentication device according to any one of supplementary notes 20, 21 and 23 wherein the control unit, in a state where the measuring object is not present in the target installation unit, acquires first spectroscopic image information including spectroscopic information for each of the areas, in a state where the measuring object is present in the target installation unit, acquires second spectroscopic image information including spectroscopic information for each of the areas, and based on the first and second spectroscopic image information, determines whether the measuring object is a living body.

[Supplementary note 25]

A biometric authentication method conducted at a device includes light irradiation means for irradiating a measuring object with a first light including a plurality of spectrums, spectroscopic means for dispersing a light at intensity depending on a wavelength and outputting the light, and image acquisition means for receiving the light output by the spectroscopic means and outputting image information representing brightness depending on the intensity of the light, the biometric authentication method includes:

for each spectrum of the first light, acquiring image information with respect to the measuring object from the image acquisition means;

based on the image information, selecting one or more areas and for each of the areas, acquiring spectroscopic information;

based on whether the spectroscopic information satisfies a predetermined condition, determining whether the measuring object is a living body; and when the measuring object is determined to be a living body, acquiring, from the image information, biological information representing a physical feature, determining whether the biological information matches with authentication biometric information registered in advance, when the biological information matches with the authentication biometric information registered in advance, determining that an authentication is successful, and when the biological information does not match with the authentication biometric information registered in advance, determining that an authentication is not successful.

[Supplementary note 26]

A biometric authentication program for causing a computer of a device includes light irradiation means for irradiating a measuring object with a first light including a plurality of spectrums, spectroscopic means for dispersing a light at intensity depending on a wavelength and outputting the light, and image acquisition means for receiving the light output by the spectroscopic means and outputting image information representing brightness depending on the intensity of the light to execute the processes of:

for each spectrum of the first light, acquiring image information with respect to the measuring object from the image acquisition means;

based on the image information, selecting one or more areas and for each of the areas, acquiring spectroscopic information;

based on whether the spectroscopic information satisfies a predetermined condition, determining whether the measuring object is a living body; and when the measuring object is determined to be a living body, acquiring, from the image information, biological information representing a physical feature, determining whether the biological information matches with authentication biometric information registered in advance, when the biological information matches with the authentication biometric information registered in advance, determining that an authentication is successful, and when the biological information does not match with the authentication biometric information registered in advance, determining that an authentication is not successful.

According to the disclosed subject matter described above, it is possible to detect the thin counterfeit, tablet terminal, and also fragments of the counterfeit and it is possible to accurately make a determination of the living body without receiving the influence of materials other than the skin.

Further, according to the disclosed subject matter, it is possible to improve the reliability of the biometric authentication and ensure the high degree of security.

This application claims priority based on Japanese Patent Application No. 2015-173737 filed on Sep. 3, 2015, the disclosure of which is incorporated herein in its entirety.

REFERENCE SIGNS LIST

3,13 Control unit
3a,13a Image processing unit
3b,13b Biometric authenticity determination unit
4 Memory
5 Input unit
6 Output unit
10 Living body determination device
13c Biometric authentication unit
101 Light irradiation device
102 Target installation device
103 Spectroscopic device
104 Image acquisition device
105 Computing device

The invention claimed is:

1. A living body determination device comprising:
at least one memory configured to store instructions; and
at least one processor configured to execute the instructions to perform:
controlling irradiation of a measuring object with a first light;
controlling a dispersing of reflected light and scattered light from the measuring object;
selecting one or more sites of the measuring object;
calculating spectroscopic image information including spectroscopic information for the one or more sites of the measuring object, the spectroscopic information representing intensity of the reflected light and the scattered light depending on a wavelength;
based on the spectroscopic image information for the one or more sites of the measuring object, determining whether the measuring object is a living body; and
when the measuring object is determined not to be a living body based on the spectroscopic image information for one site of the measuring object, then re-selecting another site of the measuring object and determining whether the measuring object is a living body based on the spectroscopic image information for the another site of the measuring object.

2. The living body determination device according to claim 1, wherein the at least one processor is further configured to execute the instructions to perform:
controlling an irradiation position of the first light based on the one or more site.

3. The living body determination device according to claim 1, wherein the at least one processor is further configured to execute the instructions to perform:
in a state where the first light is not emitted onto the measuring object, calculating first spectroscopic image information including spectroscopic information for each of the one or more site;
in a state where the first light is emitted onto the measuring object, calculating second spectroscopic image information including spectroscopic information for each of the one or more site; and
based on the first and second spectroscopic image information, determining whether the measuring object is a living body.

4. The living body determination device according to claim 1, wherein the at least one processor is further configured to execute the instructions to perform:

calculating spectroscopic information of a reference part based on an image information with respect to the reference part, the reference part being a part that reflects an incident light without changing a spectrum; and based on spectroscopic information for each of the one or more sites and the spectroscopic information of the reference part, determining whether the measuring object is a living body.

5. The living body determination device according to claim 1, wherein the at least one processor is further configured to execute the instructions to perform:

in a state where the measuring object is not present in a predetermined range, calculating first spectroscopic image information including spectroscopic information for each of the one or more sites;

in a state where the measuring object is present in the predetermined range, calculating second spectroscopic image information including spectroscopic information for each of the one or more sites; and based on the first and second spectroscopic image information, determining whether the measuring object is a living body.

6. A living body determination method, comprising:

by at least one processor, controlling irradiation of a measuring object with a first light;

controlling a dispersing of reflected light and scattered light from the measuring object;

selecting one or more sites of the measuring object;

calculating spectroscopic image information including spectroscopic information for the one or more sites of the measuring object, the spectroscopic information representing intensity of the reflected light and the scattered light depending on a wavelength;

based on the spectroscopic image information for the one or more sites of the measuring object, determining whether the measuring object is a living body; and when the measuring object is determined not to be a living body based on the spectroscopic image information for one site of the measuring object, then re-selecting another site of the measuring object and determining whether the measuring object is a living body based on the spectroscopic image information for the another site of the measuring object.

7. A non-transitory computer readable medium storing a program causing a computer to execute:

controlling irradiation of a measuring object with a first light;

controlling a dispersing of reflected light and scattered light from the measuring object;

selecting one or more sites of the measuring object;

calculating spectroscopic image information including spectroscopic information for the one or more sites of the measuring object, the spectroscopic information representing intensity of the reflected light and the scattered light depending on a wavelength; and based on the spectroscopic image information for the one or more sites of the measuring object, determining whether the measuring object is a living body; and when the measuring object is determined not to be a living body based on the spectroscopic image information for one site of the measuring object, then re-selecting another site of the measuring object and determining whether the measuring object is a living body based on the spectroscopic image information for the another site of the measuring object.

* * * * *